US011587663B2

(12) United States Patent
Mensinger et al.

(10) Patent No.: US 11,587,663 B2
(45) Date of Patent: Feb. 21, 2023

(54) INTELLIGENT MEDICATION DELIVERY SYSTEMS AND METHODS FOR MEDICINE DOSE CALCULATION AND REPORTING

(71) Applicant: MEDTRONIC MINIMED, INC., Northridge, CA (US)

(72) Inventors: Michael Mensinger, San Diego, CA (US); Sean Saint, San Diego, CA (US)

(73) Assignee: MEDTRONIC MINIMED, INC., Northridge, CA (US)

( * ) Notice: Subject to any disclaimer, the term of this patent is extended or adjusted under 35 U.S.C. 154(b) by 753 days.

(21) Appl. No.: 16/447,848

(22) Filed: Jun. 20, 2019

(65) Prior Publication Data

US 2019/0392937 A1 Dec. 26, 2019

Related U.S. Application Data

(60) Provisional application No. 62/687,669, filed on Jun. 20, 2018.

(51) Int. Cl.
*G16H 20/17* (2018.01)
*G16H 15/00* (2018.01)
(Continued)

(52) U.S. Cl.
CPC .......... *G16H 20/17* (2018.01); *A61M 5/2422* (2013.01); *A61M 5/31553* (2013.01);
(Continued)

(58) Field of Classification Search
CPC ........ G16H 20/17; G16H 40/63; G16H 40/67; G16H 15/00; G16H 50/70; G16H 20/60;
(Continued)

(56) References Cited

U.S. PATENT DOCUMENTS 4,498,904 A 2/1985 Turner et al.
4,515,584 A 5/1985 Abe et al.
(Continued)

FOREIGN PATENT DOCUMENTS

EP 0298067 4/1989
EP 513128 11/1992
(Continued)

OTHER PUBLICATIONS

Cision PR News Wire, "CompaNion Medical Announces Insights by InPen, the Future of MDI Reports", Jun. 20, 2018.
(Continued)

*Primary Examiner* — Fonya M Long
*Assistant Examiner* — Alaaeldin M Elshaer
(74) *Attorney, Agent, or Firm* — Carter, DeLuca & Farrell LLP

(57) ABSTRACT

Systems, devices, and techniques are disclosed for administering and tracking medicine to patients and providing health management capabilities for patients and caregivers. In some aspects, a system includes an injection pen device in communication with a mobile communication device having a software application to determine a recommended dose based on prior dose data, analyte data, and nutrient data and to generate a report illustrative of a relationship between the medicine data, the health data, and the contextual data.

12 Claims, 11 Drawing Sheets

(51) Int. Cl.
*A61M 5/315* (2006.01)
*A61M 5/24* (2006.01)
*A61M 5/31* (2006.01)

(52) U.S. Cl.
CPC ........ *A61M 5/31568* (2013.01); *G16H 15/00* (2018.01); *A61M 2005/3126* (2013.01); *A61M 2205/3561* (2013.01); *A61M 2205/3584* (2013.01); *A61M 2205/3592* (2013.01); *A61M 2205/50* (2013.01); *A61M 2205/502* (2013.01); *A61M 2205/52* (2013.01); *A61M 2205/583* (2013.01); *A61M 2230/06* (2013.01); *A61M 2230/201* (2013.01); *A61M 2230/30* (2013.01); *A61M 2230/63* (2013.01)

(58) Field of Classification Search
CPC ........... G16H 10/60; A61M 5/24; A61M 5/20; A61M 5/2422; A61M 5/31553; A61M 5/31568; A61M 2205/3561; A61M 2205/3584; A61M 2205/502; A61M 2230/06; A61M 2230/63; A61M 5/31546; A61M 5/31551; A61M 2005/31588; A61M 5/1723; G06F 19/3462; G06F 19/00; A61B 5/00; A61B 5/145
USPC ....................................... 705/2, 3
See application file for complete search history.

(56) References Cited

U.S. PATENT DOCUMENTS

| | | |
|---|---|---|
| 4,950,216 A | 8/1990 | Weder |
| 4,973,318 A | 11/1990 | Holm et al. |
| 4,988,660 A | 1/1991 | Campbell |
| 5,279,586 A | 1/1994 | Balkwill |
| 5,626,566 A | 5/1997 | Petersen et al. |
| 5,681,285 A | 10/1997 | Ford et al. |
| 5,822,715 A | 10/1998 | Worthington et al. |
| 5,925,021 A | 7/1999 | Castellano et al. |
| 5,984,900 A | 11/1999 | Mikkelsen |
| 6,004,297 A | 12/1999 | Steenfeldt-Jensen et al. |
| 6,042,571 A | 3/2000 | Hjertman et al. |
| 6,235,004 B1 | 5/2001 | Steenfeldt-Jensen et al. |
| 6,302,855 B1 | 10/2001 | Lav et al. |
| 6,482,185 B1 | 11/2002 | Hartmann |
| 6,817,986 B2 | 11/2004 | Slate et al. |
| 7,591,801 B2 | 9/2009 | Brauker et al. |
| 7,905,833 B2 | 3/2011 | Brister et al. |
| 7,955,303 B2 | 6/2011 | Burren et al. |
| 7,976,492 B2 | 7/2011 | Brauker et al. |
| 8,221,356 B2 | 7/2012 | Enggaard et al. |
| 8,229,535 B2 | 7/2012 | Mensinger et al. |
| 8,231,531 B2 | 7/2012 | Brister et al. |
| RE43,834 E | 11/2012 | Steenfeldt-Jensen et al. |
| 8,460,231 B2 | 6/2013 | Brauker et al. |
| 8,565,848 B2 | 10/2013 | Brister et al. |
| D694,252 S | 11/2013 | Helm |
| 8,591,455 B2 | 11/2013 | Mensinger et al. |
| 8,663,109 B2 | 3/2014 | Brister et al. |
| 8,721,585 B2 | 5/2014 | Mensinger et al. |
| 8,750,955 B2 | 6/2014 | Mensinger et al. |
| 8,808,228 B2 | 8/2014 | Brister et al. |
| 8,882,741 B2 | 11/2014 | Brauker et al. |
| 8,920,401 B2 | 12/2014 | Brauker et al. |
| 8,926,585 B2 | 1/2015 | Brauker et al. |
| D727,928 S | 4/2015 | Allison et al. |
| 9,020,572 B2 | 4/2015 | Mensinger et al. |
| 9,050,413 B2 | 6/2015 | Brauker et al. |
| D738,385 S | 9/2015 | Lim et al. |
| 9,143,569 B2 | 9/2015 | Mensinger et al. |
| 9,155,843 B2 | 10/2015 | Brauker et al. |
| D747,333 S | 1/2016 | Supino et al. |
| D748,101 S | 1/2016 | Bang et al. |
| D748,126 S | 1/2016 | Sarukkai et al. |
| D749,103 S | 2/2016 | Song |
| D753,685 S | 4/2016 | Zimmerman et al. |
| D754,689 S | 4/2016 | Lee |
| D759,684 S | 6/2016 | Bijlani et al. |
| D761,280 S | 7/2016 | Chung et al. |
| D763,308 S | 8/2016 | Wang et al. |
| D766,958 S | 9/2016 | Salazar Cardozo et al. |
| 9,446,194 B2 | 9/2016 | Kamath et al. |
| D777,760 S | 1/2017 | Zhao et al. |
| D781,890 S | 3/2017 | Gathman et al. |
| D783,037 S | 4/2017 | Hariharan et al. |
| D783,648 S | 4/2017 | Vazquez et al. |
| D784,391 S | 4/2017 | Yuguchi et al. |
| D785,025 S | 4/2017 | Zimmerman et al. |
| D786,273 S | 5/2017 | Herman et al. |
| 9,672,328 B2 | 6/2017 | Saint |
| D791,806 S | 7/2017 | Brewington et al. |
| D794,047 S | 8/2017 | Gandhi et al. |
| D795,900 S | 8/2017 | Bischoff et al. |
| D795,919 S | 8/2017 | Bischoff et al. |
| D795,927 S | 8/2017 | Bischoff et al. |
| D797,760 S | 9/2017 | Tsujimura et al. |
| D798,312 S | 9/2017 | Tsujimura et al. |
| 9,775,543 B2 | 10/2017 | Brister et al. |
| D808,986 S | 1/2018 | Dudey |
| D809,544 S | 2/2018 | Ambielli |
| D809,545 S | 2/2018 | Ban et al. |
| D811,425 S | 2/2018 | Olsen et al. |
| D815,127 S | 4/2018 | Phillips et al. |
| D815,667 S | 4/2018 | Yeung |
| 9,937,293 B2 | 4/2018 | Brauker et al. |
| D819,043 S | 5/2018 | Yamaura et al. |
| D820,297 S | 6/2018 | Gardner et al. |
| 9,996,668 B2 | 6/2018 | Reihman et al. |
| D831,049 S | 10/2018 | Agarwal et al. |
| D831,684 S | 10/2018 | Ghosh |
| D832,292 S | 10/2018 | Hu et al. |
| D832,870 S | 11/2018 | Hu |
| D833,469 S | 11/2018 | Coleman et al. |
| D835,118 S | 12/2018 | Lee et al. |
| D837,807 S | 1/2019 | Baber et al. |
| D838,734 S | 1/2019 | Kruse et al. |
| 10,169,539 B2 | 1/2019 | Reihman et al. |
| D842,888 S | 3/2019 | Krainer et al. |
| D843,402 S | 3/2019 | Casse et al. |
| D846,590 S | 4/2019 | Cabrera et al. |
| D847,165 S | 4/2019 | Cheney et al. |
| D849,757 S | 5/2019 | Jing et al. |
| 10,278,580 B2 | 5/2019 | Brister et al. |
| 2003/0065536 A1 | 4/2003 | Hansen et al. |
| 2004/0039255 A1 | 2/2004 | Simonsen et al. |
| 2005/0038674 A1 | 2/2005 | Braig et al. |
| 2005/0049179 A1 | 3/2005 | Davidson et al. |
| 2005/0182358 A1 | 8/2005 | Veit et al. |
| 2005/0192494 A1 | 9/2005 | Ginsberg |
| 2005/0192557 A1 | 9/2005 | Brauker et al. |
| 2006/0036144 A1 | 2/2006 | Brister et al. |
| 2006/0173417 A1 | 8/2006 | Rosen et al. |
| 2007/0021715 A1 | 1/2007 | Kohlbrenner et al. |
| 2007/0038044 A1 | 2/2007 | Dobbles et al. |
| 2007/0173708 A9 | 7/2007 | Dobbles et al. |
| 2007/0186923 A1 | 8/2007 | Poutiatine et al. |
| 2007/0239486 A1 | 10/2007 | Gordon |
| 2008/0071580 A1* | 3/2008 | Marcus ................. G16H 20/17 705/3 |
| 2008/0162192 A1 | 7/2008 | Vonk et al. |
| 2008/0188813 A1 | 8/2008 | Miller et al. |
| 2008/0201169 A1 | 8/2008 | Galasso et al. |
| 2008/0234663 A1 | 9/2008 | Yodfat et al. |
| 2008/0235053 A1 | 9/2008 | Ray et al. |
| 2008/0262469 A1 | 10/2008 | Brister et al. |
| 2009/0036771 A1 | 2/2009 | Fago et al. |
| 2009/0048561 A1 | 2/2009 | Burren et al. |
| 2009/0069742 A1 | 3/2009 | Larsen |
| 2009/0131875 A1 | 5/2009 | Green |
| 2009/0163793 A1 | 6/2009 | Koehler |
| 2009/0209938 A1 | 8/2009 | Aalto-Setala |
| 2009/0216103 A1 | 8/2009 | Brister et al. |
| 2009/0240120 A1 | 9/2009 | Mensinger et al. |

(56) References Cited

U.S. PATENT DOCUMENTS

| | | |
|---|---|---|
| 2009/0240128 A1 | 9/2009 | Mensinger et al. |
| 2009/0240193 A1 | 9/2009 | Mensinger et al. |
| 2009/0299276 A1 | 12/2009 | Brauker et al. |
| 2010/0049126 A1 | 2/2010 | Bronfeld et al. |
| 2010/0063438 A1 | 3/2010 | Bengtsson |
| 2010/0081993 A1 | 4/2010 | O'Connor |
| 2010/0094251 A1* | 4/2010 | Estes ............ A61M 5/1723 604/504 |
| 2010/0185075 A1 | 7/2010 | Brister et al. |
| 2010/0261987 A1 | 10/2010 | Kamath et al. |
| 2010/0331656 A1 | 12/2010 | Mensinger et al. |
| 2010/0331657 A1 | 12/2010 | Mensinger et al. |
| 2011/0009727 A1 | 1/2011 | Mensinger et al. |
| 2011/0264033 A1 | 10/2011 | Jensen et al. |
| 2011/0270158 A1 | 11/2011 | Brauker et al. |
| 2011/0275986 A1 | 11/2011 | Bashan |
| 2011/0281791 A1 | 11/2011 | Zion et al. |
| 2011/0313349 A1 | 12/2011 | Krulevitch et al. |
| 2011/0313350 A1 | 12/2011 | Krulevitch et al. |
| 2011/0313395 A1 | 12/2011 | Krulevitch et al. |
| 2012/0072236 A1 | 3/2012 | Atkin |
| 2012/0186581 A1 | 7/2012 | Brauker et al. |
| 2012/0190953 A1 | 7/2012 | Brauker et al. |
| 2012/0191063 A1 | 7/2012 | Brauker et al. |
| 2012/0215201 A1 | 8/2012 | Brauker et al. |
| 2012/0220979 A1 | 8/2012 | Brauker et al. |
| 2012/0238852 A1 | 9/2012 | Brauker et al. |
| 2012/0296311 A1 | 11/2012 | Brauker et al. |
| 2013/0035575 A1 | 2/2013 | Mayou et al. |
| 2013/0035865 A1 | 2/2013 | Mayou et al. |
| 2013/0035871 A1 | 2/2013 | Mayou et al. |
| 2013/0171938 A1 | 7/2013 | Mears et al. |
| 2013/0184996 A1 | 7/2013 | Zivitz et al. |
| 2013/0197445 A1 | 8/2013 | Schabbach et al. |
| 2013/0197479 A1 | 8/2013 | Butler et al. |
| 2013/0211248 A1 | 8/2013 | Cowan et al. |
| 2013/0291116 A1 | 10/2013 | Homer |
| 2014/0012117 A1 | 1/2014 | Mensinger et al. |
| 2014/0012118 A1 | 1/2014 | Mensinger et al. |
| 2014/0012510 A1 | 1/2014 | Mensinger et al. |
| 2014/0012511 A1 | 1/2014 | Mensinger et al. |
| 2014/0074041 A1 | 3/2014 | Pedersen et al. |
| 2014/0113856 A1 | 4/2014 | Pohl et al. |
| 2014/0114158 A1 | 4/2014 | Brister et al. |
| 2014/0114161 A1 | 4/2014 | Kamath et al. |
| 2014/0257065 A1 | 9/2014 | Walsh |
| 2014/0276531 A1 | 9/2014 | Walsh |
| 2014/0288494 A1 | 9/2014 | Brister et al. |
| 2015/0073337 A1 | 3/2015 | Saint et al. |
| 2015/0202377 A1 | 7/2015 | Haupt |
| 2015/0351683 A1 | 12/2015 | Brauker et al. |
| 2015/0359965 A1 | 12/2015 | O'Connor et al. |
| 2016/0012205 A1* | 1/2016 | Saint ............ A61M 5/31528 604/189 |
| 2016/0030683 A1 | 2/2016 | Taylor |
| 2016/0066843 A1 | 3/2016 | Mensinger et al. |
| 2016/0081632 A1 | 3/2016 | Kamath et al. |
| 2016/0101232 A1 | 4/2016 | Kamath et al. |
| 2017/0068799 A1 | 3/2017 | Mensinger et al. |
| 2017/0124272 A1 | 5/2017 | Reihman et al. |
| 2017/0124275 A1 | 5/2017 | Reihman et al. |
| 2017/0124350 A1 | 5/2017 | Reihman et al. |
| 2017/0131993 A1 | 5/2017 | Salameh et al. |
| 2017/0132120 A1 | 5/2017 | Salameh et al. |
| 2017/0185283 A1 | 6/2017 | Bhavaraju et al. |
| 2017/0185284 A1 | 6/2017 | Bhavaraju et al. |
| 2017/0189625 A1 | 7/2017 | Cirillo et al. |
| 2017/0270276 A1 | 9/2017 | Saint et al. |
| 2017/0286194 A1 | 10/2017 | Morris et al. |
| 2017/0286614 A1 | 10/2017 | Morris et al. |
| 2017/0366617 A1 | 12/2017 | Mensinger et al. |
| 2017/0367627 A1 | 12/2017 | Brister et al. |
| 2018/0185587 A1 | 7/2018 | Brauker et al. |
| 2018/0303417 A1 | 10/2018 | Mensinger et al. |
| 2018/0353698 A1 | 12/2018 | Saint et al. |
| 2019/0015020 A1 | 1/2019 | Brister et al. |
| 2019/0035500 A1 | 1/2019 | Saint et al. |
| 2019/0132801 A1 | 5/2019 | Kamath et al. |
| 2019/0173885 A1 | 6/2019 | Kamath et al. |
| 2019/0125224 A1 | 8/2019 | Kamath et al. |

FOREIGN PATENT DOCUMENTS

| | | |
|---|---|---|
| EP | 927057 | 7/1999 |
| EP | 2572740 | 3/2013 |
| WO | 9638190 | 12/1996 |
| WO | 2010052275 | 5/2010 |
| WO | 2011041007 | 4/2011 |
| WO | 2012046199 | 4/2012 |
| WO | 2013053695 | 4/2013 |
| WO | 2014128157 | 8/2014 |
| WO | 2015047870 | 4/2015 |
| WO | 2015169814 | 11/2015 |
| WO | 2015185686 | 12/2015 |
| WO | 2016071912 | 5/2016 |
| WO | 2017132577 | 3/2018 |

OTHER PUBLICATIONS

Copenheaver, B. R., Authorized Officer, ISA/US, International Search Report and Written Opinion, International Application No. PCT/US2014/056336, dated Dec. 31, 2014, 10 pages.

Young, Lee W., ISA/US, International Search Report, International Application No. PCT/US15/40069, dated Dec. 22, 2015, 13 pages.

Young, Lee W., ISA/US, Invitation to Pay Additional Fees and Partial Search Report, International Application No. PCT/US15/40069, dated Oct. 1, 2015, 2 pages.

Extended European Search Report for European Patent Application No. 14849422.2, dated May 4, 2017, 11 pages.

International Search Report and Written Opinion for PCT Application No. PCT/US2018/036768; dated Aug. 31, 2018, 10 pages.

International Search Report and Written Opinion for PCT Application No. PCT/US2017/15452, dated May 23, 2017, 14 pages.

Extended European Search Report for European Patent Application No. 17745019.4, dated Aug. 6, 2019, 9 pages.

International Search Report and Written Opinion for PCT Application No. PCT/US2018/55646, dated Feb. 6, 2019, 15 pages.

* cited by examiner

INTELLIGENT MEDICATION DELIVERY SYSTEMS AND METHODS FOR MEDICINE DOSE CALCULATION AND REPORTING

CROSS-REFERENCE TO RELATED APPLICATIONS

This patent document claims priorities to and benefits of U.S. Provisional Patent Application No. 62/687,669 entitled "INTELLIGENT MEDICATION DELIVERY SYSTEMS AND METHODS FOR MEDICINE DOSE CALCULATION AND REPORTING" filed on Jun. 20, 2018. The entire content of the aforementioned patent application is incorporated by reference as part of the disclosure of this patent document.

TECHNICAL FIELD

This patent document relates to medicine administering and tracking systems, devices, and processes.

BACKGROUND

Diabetes mellitus, also referred to as diabetes, is a metabolic disease associated with high blood sugar due to insufficient production or use of insulin by the body. Diabetes is widely-spread globally, affecting hundreds of millions of people, and is among the leading causes of death globally. Diabetes has been categorized into three categories or types: type 1, type 2, and gestational diabetes. Type 1 diabetes is associated with the body's failure to produce sufficient levels of insulin for cells to uptake glucose. Type 2 diabetes is associated with insulin resistance, in which cells fail to use insulin properly. The third type of diabetes is commonly referred to as gestational diabetes, which can occur during pregnancy when a pregnant woman develops a high blood glucose level. Gestational diabetes can develop into type 2 diabetes, but often resolves after the pregnancy.

SUMMARY

Systems, devices, and techniques are disclosed for administering and tracking medicine to patients and providing health management capabilities for patients and caregivers.

In some aspects, an intelligent medicine administering system includes a smart insulin injection pen in wireless communication with a patient's companion device (e.g., smartphone) operating a software application (app), which provides dose calculator and decision support modules that calculate and recommend a time- and context-sensitive dose of medicine (e.g., insulin) the user should administer based on a 'titration protocol' using retrospective and predictive data from insulin reports generated by the app.

In some aspects, a system for tracking a dose of a medicine to a patient includes an injection pen device including a dose setting mechanism to set a dose of a medicine contained in a medicine cartridge that is to be dispensed by the injection pen device, a dispensing mechanism to dispense the medicine according to the set dose, and electronic circuits including a processor, a memory comprising instructions executable by the processor, and a wireless transmitter, the processor of the injection pen device configured to generate dose data associated with a dispensing event of a dose of the medicine dispensed from the injection pen device and time data associated with the dispensing event, and to wirelessly transmit the dose data; the injection pen device is in wireless communication with a mobile communication device that includes a data processing unit including a processor and memory to receive and process the dose data, wherein the mobile communication device includes a software application program product comprising a non-transitory computer-readable storage medium having instructions, which when executed by the processor of the data processing unit, cause the mobile communication device to determine a recommended dose based on medicine data including dose data on one or more prior medicine doses, health data and contextual data associated with a user of the injection pen device, wherein the health data includes analyte data, and the contextual data includes nutrient data corresponding to a food, wherein the software application program product includes a data aggregator that obtains the health data and the contextual data, a dose calculator that autonomously determines the recommended dose of the medicine, and a report generator that generates a report that is displayable on a display of the mobile communication device and that is illustrative of a relationship between the medicine data, the health data, and the contextual data, wherein the report generator formats the report to include the medicine data, the analyte data, and the nutrient data each represented by a graphical indicator plotted on a single graph such that the graphical indicators associated with the medicine data and the nutrient data are spatially aligned and sized with the graphical indicator associated with the analyte data based on (i) temporal information of the medicine data, the analyte data, and the nutrient data and (ii) a dynamic trend of the analyte data that determines a size of the graphical indicators associated with the medicine data and the nutrient data scaled to a rate of change of the dynamic trend.

In some aspects, a system for determining a dose of a medicine to a patient includes an injection pen device including a dose setting mechanism to set a dose of a medicine contained in a medicine cartridge that is to be dispensed by the injection pen device, a dispensing mechanism to dispense the medicine according to the set dose, and electronic circuits including a processor, a memory comprising instructions executable by the processor, and a wireless transmitter, the processor of the injection pen device configured to generate dose data associated with a dispensing event of a dose of the medicine dispensed from the injection pen device and time data associated with the dispensing event, and to wirelessly transmit the dose data; the injection pen device is in wireless communication with a mobile communication device that includes a data processing unit including a processor and memory to receive and process the dose data, wherein the mobile communication device includes a software application program product comprising a non-transitory computer-readable storage medium having instructions, which when executed by the processor of the data processing unit, cause the mobile communication device to determine a recommended dose based on medicine data including dose data on one or more prior medicine doses, health data and contextual data associated with a user of the injection pen device, wherein the health data includes analyte data, and the contextual data includes physical activity data and/or nutrient data corresponding to a food, wherein the software application program product includes a data aggregator that obtains the health data and the contextual data, a dose calculator that autonomously determines the recommended dose of the medicine, and a user interface generator that produces a user interface on a display of the mobile communication device that displays, on the produced user interface, the recommended dose, wherein dose calculator autonomously modifies the determined recommended dose of the medicine when the determined recommended dose was not administered by the injection pen device in a predetermined time period from display of the recommended dose to qualify as a missed dose, and wherein the user interface generator produces the user interface to include an indication of the missed dose.

DETAILED DESCRIPTION

Figure 1A:
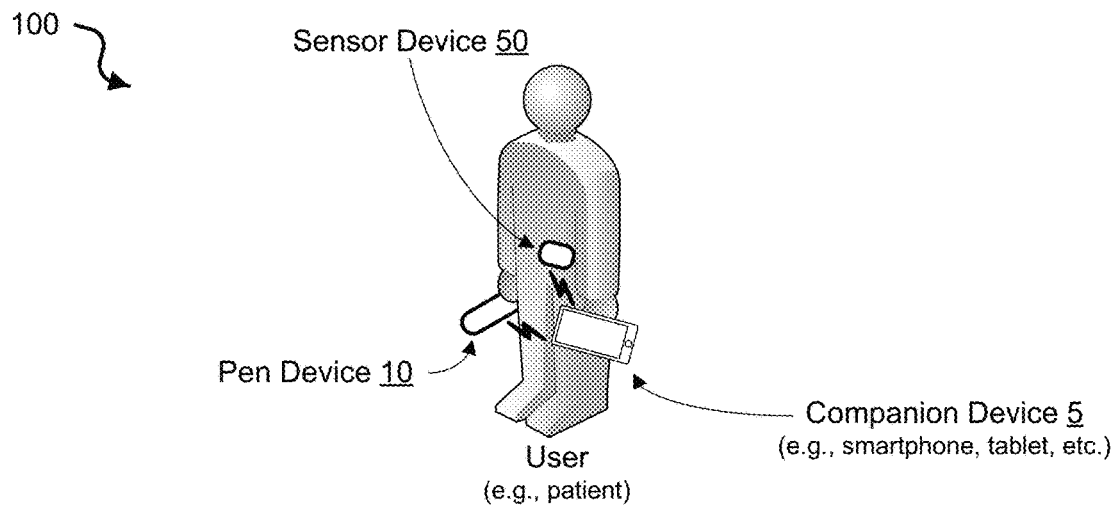
FIG. 1A shows a diagram of an example embodiment of an intelligent medicine administering system in accordance with the present technology.

Various diseases and medical conditions, such as diabetes, require a patient to self-administer doses of a fluid medication. Typically, when administering a fluid medication, the appropriate dose amount is set and dispensed by the patient using a syringe, a pen, or a pump. For example, self-administered medicaments or medicine include insulin used to treat diabetes, Follistim® used to treat infertility, or other injectable medicines such as Humira®, Enbrel®, Lovenox® and Ovidrel®, or others.

A medicament pen is a device that can be used to inject a quantity of a medicine (e.g., single or multiple boluses or doses of the medicine) into a user's body, where more than one dose can be stored in a medicine cartridge contained in the pen device. Pens offer the benefit of simplicity over other methods of delivery, such as syringe or pump-based methods. For example, syringes typically require more steps to deliver a dose, and pumps typically are more complicated to use and require a constant tether to the patient. However, previously there has not been an automated way to track and communicate the doses given with the pen in a simple, effective and reliable manner. In addition, it can be difficult to know how much to dose with the pen, when to dose, or if the patient dosed at all.

As with the dosing of any medication, it is sometimes hard for a patient to remember if a dose has been given. For this reason, for example, pill reminders have been developed where the patient places the medication for the day in a cup labeled with that day. Once they take their medication, there is no question it has been taken because the pills are no longer in the cup. Yet, there are no widely acceptable solutions that address this problem for injection-based therapies. Therefore, without simple, effective and reliable ways of tracking medicine doses, particularly for managing lifelong or chronic conditions like diabetes, patients may easily miss a dose or administer an incorrect dose (e.g., under-dose or over-dose) of their medicine which may result in serious, dangerous consequences to their health.

In addition to the challenges of tracking doses, calculating the right dose at the right time or under the right conditions is a widespread problem for patients of chronic conditions requiring daily dosing of medicine. Conventional dose calculators for administering insulin for Type I and Type II diabetes typically require manual estimation of carbohydrates ("carbs") at mealtime. For some users, carb counting and estimating may be too difficult, and some users may not utilize the dose calculator due to the manual work and number of steps required to do so, e.g., taking out one's smartphone, opening up an app, manually typing calculator inputs, etc.

Moreover, conventional bolus or basal insulin dose calculators are designed to operate using a pre-set, fixed dosing parameters that inform the dose calculator, as defined by a physician. Primary variables of insulin dose are just the user's analyte levels, food intake, and insulin on board. Yet, there are countless other factors that affect the user's glucose and insulin responses, some of which can be incorporated into refined dosing parameters.

Disclosed are intelligent medicine administering systems and methods that provide enhanced medicine dose recommendations for patient health management by the patient and their caregivers using medicine injection devices.

In some embodiments in accordance with the present technology, an intelligent medicine administering system provides medicine dose recommendation and management capabilities for Type I and Type II diabetes patients and their caregivers. In some aspects, an intelligent medicine administering system includes a medicine injection device (e.g., insulin pen, also referred to as a "pen" or "pen device"), in wireless communication with a patient's companion device (e.g., smartphone). The companion device includes a software application ("app") having a dose calculator and decision support modules to calculate and recommend the dose of a medicine (e.g., insulin) the patient should administer using the wirelessly connected medicine injection device, as well as to provide control over several functionalities of the medicine injection device, e.g., such as encoding and processing the signals associated with dose sizes for injection. In various embodiments, the dose calculator is configured as an adaptive dose calculator able to calculate and recommend a time- and context-sensitive dose of the medicine (e.g., insulin) based on a titration protocol using retrospective and predictive data extracted from insulin reports generated by the app.

Communication between the pen device and the companion device provides the ability for dose tracking, logging, calculating, recommending and/or communicating of dose data with a user (e.g., patient user, health care provider (HCP) and/or caregiver), and other advantages of the intelligent medicine administering system. For example, each bolus that is dispensed by the pen device can be automatically logged and communicated to the companion device.

FIG. 1A shows a diagram of an example embodiment of an intelligent medicine administering system 100 in accordance with the present technology. The system 100 includes a pen device 10 in wireless communication with a mobile computing and communication device 5 of a patient user, also referred to as the user's companion device. The pen device 10 is operable to select, set and/or dispense a dose of the medicine for dispensing. In some implementations, the companion device 5 includes a smartphone, tablet, and/or wearable computing device, such as a smartwatch, smart-glasses, etc. In some implementations, the companion device 5 is in communication with other computing devices, such as a laptop and/or desktop computer, a smart television, or network-based server computer. The companion device 5 includes an app associated with the pen device 10 of the intelligent medicine administering system 100, which can monitor and/or control functionalities of the pen device 10 and to provide a dose calculator and/or decision support modules that can calculate and recommend a dose of the medicine for the patient user to administer using the pen device 10.

The companion device 5 can be used to obtain, process and/or display contextual data that can be used to relate to the patient user's health condition, including the condition for which the pen device 10 is used to treat. In an illustrative example, the companion device 5 is operable to track the patient user's location; the patient user's physical activity including step count, movement distance and/or intensity, estimated calories burned, and/or activity duration; and/or the patient user's interaction pattern with the companion device 5. The app associated with the system 100 can aggregate and process the contextual data to generate decision support outputs to guide and aid the patient user in using the pen device 10 and/or managing their behavior to promote better health outcomes in treating his/her health condition.

In some embodiments, the system 100 includes a sensor device 50 to monitor one or more health metrics of the patient user. Examples of health metric data monitored by the sensor device 50 include analytes, such as glucose, heart rate, blood pressure, user movement, or other. In some implementations, the sensor device 50 is a wearable sensor device such as a continuous glucose monitor (CGM) to obtain transcutaneous or blood glucose measurements that are processed to produce continuous glucose values. For example, the continuous glucose monitor can include a glucose processing module implemented on a stand-alone display device and/or implemented on the companion device 5, which processes, stores and displays the continuous glucose values for the patient user.

Figure 1B:
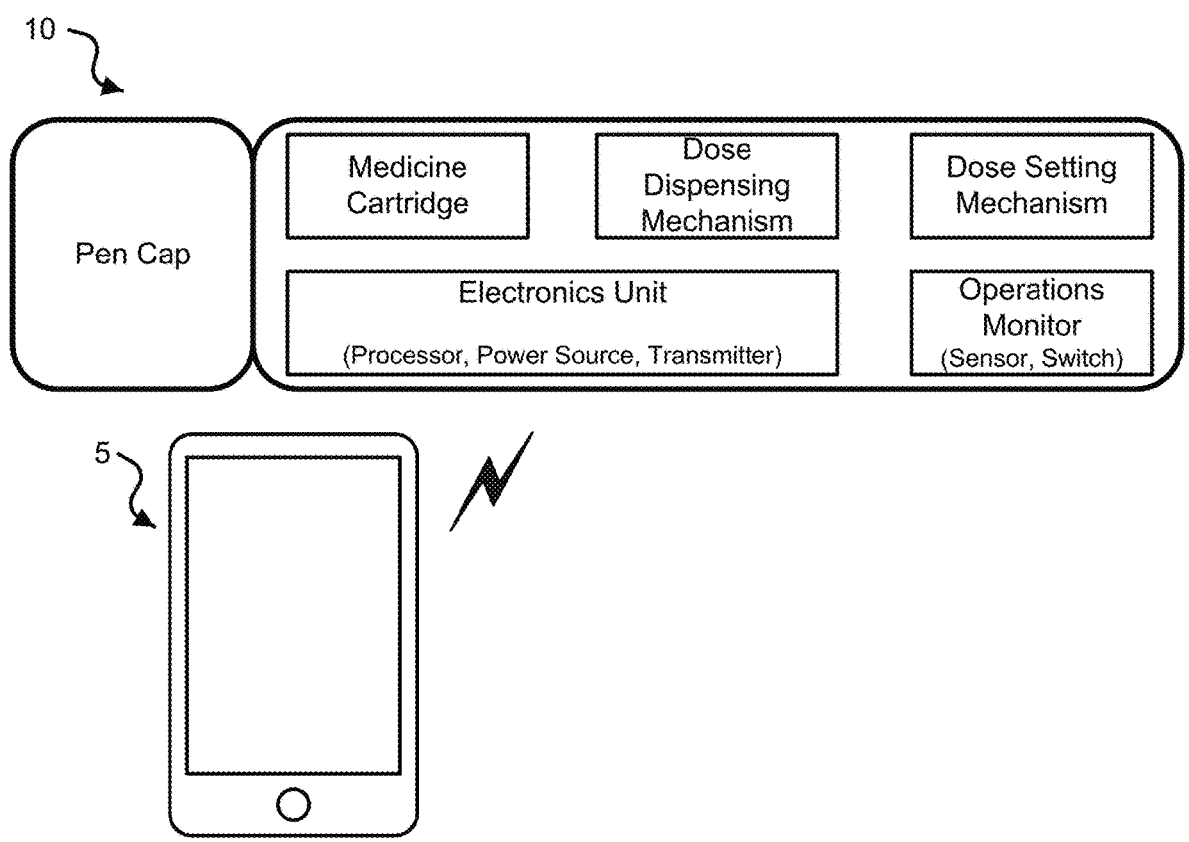
FIG. 1B shows a diagram of an example embodiment of a pen device in communication with a companion device of the intelligent medicine administering system of FIG. 1A.

FIG. 1B shows a diagram of an example embodiment of the pen device 10 of the intelligent medicine administering system 100. The pen device 10 is structured to have a body which contains the medicine cartridge (e.g., which can be replaceable). The pen device 10 is structured to include a dose dispensing mechanism to dispense (e.g., deliver) the medicine contained in the medicine cartridge out of the pen device 10; a dose setting mechanism to select and/or set the dose to be dispensed; an operations monitoring mechanism to determine that the pen device is being operated and/or to monitor the operation of the dose being dispensed (e.g., such as a switch and/or sensor, or an encoder); and an electronics unit that can include a processor, a memory, a battery or other power source, and a transmitter.

The pen device 10 is configured in communication with the patient user's mobile computing and communication device 5, e.g., such as the user's smartphone, tablet, and/or wearable computing device, such as a smartwatch, smart-glasses, etc., and/or a user's laptop and/or desktop computer, a smart television, or network-based server computer.

In some implementations of the system 100, for example, to use the pen device 10, the user first dials up a dose using a dose knob. The dose knob of the pen device 10 can be included as part of the dose setting mechanism and/or the dose dispensing mechanism. For example, the dose may be adjusted up or down prior to administration of the dose. When the user applies a force against a dose dispensing button (e.g., presses against the dose dispensing button that is caused to protrude outward from the pen's body upon dialing the dose using the dose knob), a pushing component (e.g., also referred to as a 'plunger') of the dose dispensing mechanism is depressed against an abutment of the medicine cartridge loaded in the pen device 10 to cause the pen device 10 to begin to dispense the medicine, in which the quantity dispensed is in accordance with that set by the dose setting mechanism. In such implementations, the operations monitoring mechanism of the pen device 10 will begin to sense movement of a rotating component or shaft that drives the plunger, for example, in which the movement is sensed through an encoder. In some examples, the encoder can be configured to sense the rotation of a component that is coupled to the drive shaft, and as the drive shaft rotates the plunger moves linearly; and therefore by sensing rotation of the component, the movement of the drive shaft and the plunger is sensed. Movement of the encoder may be detected as data processed by a processor of the electronics unit of the pen device 10, which can be used to measure the dose. In some implementations, the processor can then store the size of the dose along with a time stamp for that dose. In some implementations, the pen device 10 can then transmit the dose and related information to the companion device 5. In such implementations when the dose is transmitted, the data associated with the particular transmitted dose is marked in the memory of the pen device 10 as transmitted. In such implementations if the dose was not yet transmitted to the companion device 5, then the data associated with the dose will be transmitted at the next time a successful communication link between the pen device 10 and the companion device 5 is established.

The operations monitoring mechanism of the pen device 10 can include a sensor that can utilize any method of sensing rotary or linear movement. Non-limiting examples of such sensors include rotary and linear encoders, Hall effect and other magnetic based sensors, linearly variable displacement transducers, or any other appropriate method of sensing known in the art.

The dose dispensing mechanism of the pen device 10 can include a manually powered mechanism or a motorized mechanism. In either case, a force (e.g., either produced by the patient or by an electrically-powered motor) pushes on the plunger of the dose dispensing mechanism to in turn force a receiving plunger of the medicament vial or cartridge to deliver the specific amount of the medicament. In some implementations, for example, the dose dispensing mechanism can be adjusted to deliver the dose over a different period of time. In one example, the dose dispensing mechanism can be operated such that the plunger is pushed in by an adjustable tension spring or change the speed of the motor to inject the dose over a time frame (e.g., 1 s, 5 s or other)

to aid in reducing the pain of dosing. In one example, the dose dispensing mechanism can be operated over a much longer period of time, e.g., to better match the dynamics of carbohydrates, which can be like an extended bolus with a pump.

The software application (app) of the companion device 5 associated with the pen device 10 provides a user interface to allow the user to manage his/her health-related data. In some implementations, for example, the companion device 5 can be configured to control some functionalities of the pen device 10. In some implementations, for example, the companion device 5 includes the user's existing smartphone, tablet, or wearable computing device. In some implementations, for example, the companion device 5 is an independent portable device that the user may carry on his/her person. In one example embodiments of an independent portable companion device 5, the companion device 5 includes a data processing unit, wireless communication unit to allow the device to communicate with the pen device 10, and a display unit.

Figure 1C:
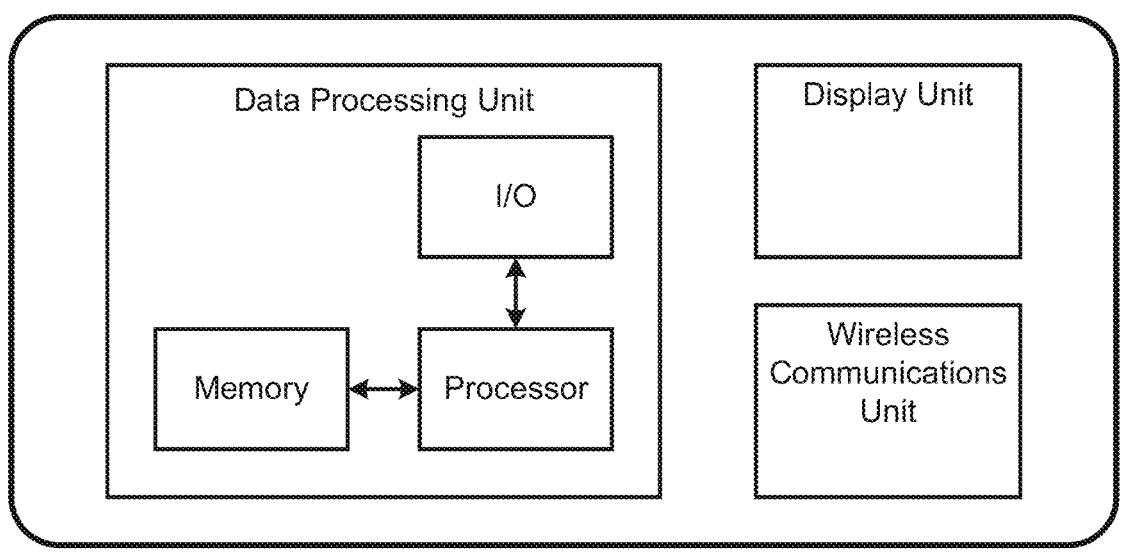
FIG. 1C shows a block diagram of an example embodiment of the companion device of the intelligent medicine administering system of FIG. 1A.

FIG. 1C shows a block diagram of an example embodiment of the companion device 5 of the intelligent medicine administering system 100. The data processing unit of the companion device 5 includes a processor to process data, a memory in communication with the processor to store data, and an input/output unit (I/O) to interface the processor and/or memory to other modules, units or devices of the companion device 5 or external devices. For example, the processor can include a central processing unit (CPU) or a microcontroller unit (MCU). For example, the memory can include and store processor-executable code, which when executed by the processor, configures the data processing unit to perform various operations, e.g., such as receiving information, commands, and/or data, processing information and data, and transmitting or providing information/data to another device. In some implementations, the data processing unit can transmit raw or processed data to a computer system or communication network accessible via the Internet (referred to as 'the cloud') that includes one or more remote computational processing devices (e.g., servers in the cloud). To support various functions of the data processing unit, the memory can store information and data, such as instructions, software, values, images, and other data processed or referenced by the processor. For example, various types of Random Access Memory (RAM) devices, Read Only Memory (ROM) devices, Flash Memory devices, and other suitable storage media can be used to implement storage functions of the memory unit. The I/O of the data processing unit can interface the data processing unit with the wireless communications unit to utilize various types of wired or wireless interfaces compatible with typical data communication standards, for example, which can be used in communications of the data processing unit with other devices such as the pen device 10, via a wireless transmitter/receiver (Tx/Rx) unit, e.g., including, but not limited to, Bluetooth, Bluetooth low energy, Zigbee, IEEE 802.11, Wireless Local Area Network (WLAN), Wireless Personal Area Network (WPAN), Wireless Wide Area Network (WWAN), WiMAX, IEEE 802.16 (Worldwide Interoperability for Microwave Access (WiMAX)), 3G/4G/LTE cellular communication methods, NFC (Near Field Communication), and parallel interfaces. The I/O of the data processing unit can also interface with other external interfaces, sources of data storage, and/or visual or audio display devices, etc. to retrieve and transfer data and information that can be processed by the processor, stored in the memory unit, or exhibited on an output unit of the companion device 5 or an external device. For example, a display unit of the companion device 5 can be configured to be in data communication with the data processing unit, e.g., via the I/O, to provide a visual display, an audio display, and/or other sensory display that produces the user interface of the software application of the disclosed technology for health management. In some examples, the display unit can include various types of screen displays, speakers, or printing interfaces, e.g., including but not limited to, light emitting diode (LED), or liquid crystal display (LCD) monitor or screen, cathode ray tube (CRT) as a visual display; audio signal transducer apparatuses as an audio display; and/or toner, liquid inkjet, solid ink, dye sublimation, inkless (e.g., such as thermal or UV) printing apparatuses, etc.

In various operations of the intelligent medicine administering system 100, for example, when a dosing event (e.g., an amount of fluid is dispensed from the pen device 10), a time stamp associated with the dispensing is referenced is recorded by the processing unit of the pen device 10 (e.g., stored in the memory of the pen device 10). For example, the time stamp may be the current time or a time where a count-up timer is used. When the dose information is eventually transmitted to the companion device 5, the time stamp and/or a 'time-since-dose' parameter is transmitted by the pen device 10 and received by the companion device 5 and stored in the memory of the data processing unit of the companion device 5. In some implementations, for example, the time of the dose can be determined without the pen having to know the current time. This can simplify operation and setup of the pen device 10. In some implementations, for example, a user time is initialized on the pen device 10 from the companion device 5, in which the user time is used for dose time tracking. Using the system 100, the companion device 5 can know the time of the dose relative to the current time.

Once the companion device 5 receives the dose related information (e.g., which can include the time information and dose setting and/or dispensing information, and other information about the pen device 10 related to the dosing event), the companion device 5 stores the dose related information in memory, e.g., which can include among a list of doses or dosing events. For example, via the software application's user interface, the companion device 5 allows the patient to browse a list of previous doses, to view an estimate of current medicament active in the patient's body ("medicament on board") based on calculations performed by a medicine calculation module of the software application, and/or to utilize a dose calculation module of the software application to assist the patient regarding dose setting information on the size of the next dose to be delivered. For example, the patient could enter carbohydrates to be eaten, current blood sugar, and the companion device 5 would already know insulin on board. Using these parameters, a suggested medicine dose (e.g., such as insulin dose), calculated by the dose calculation module, may be determined. In some implementations, for example, the companion device 5 can also allow the patient to manually enter boluses into the pen device 10 or another medicine delivery device. This would be useful if the patient was forced to use a syringe, or if the battery in the pen device 10 was depleted.

Figure 1D:
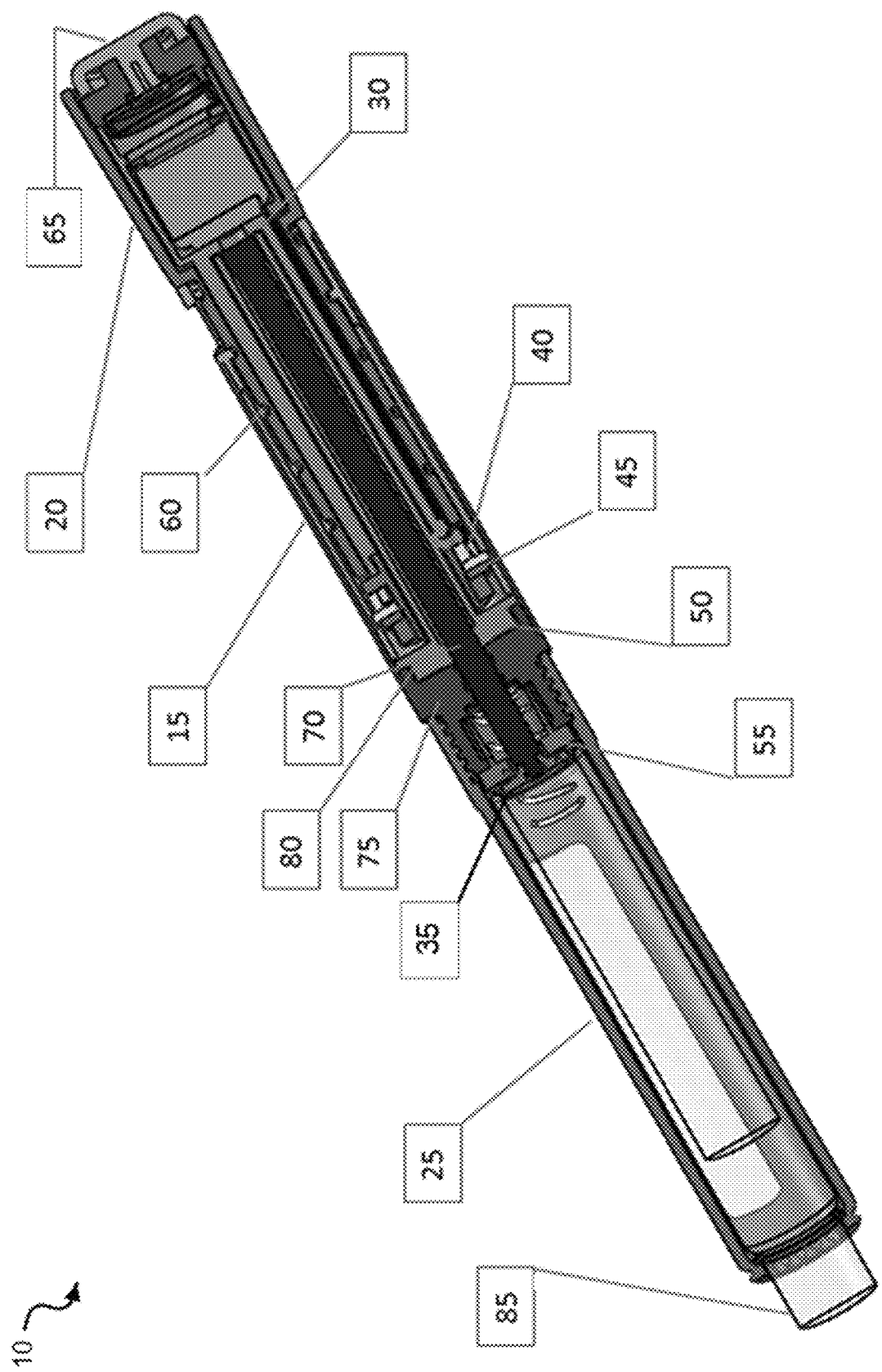
FIG. 1D shows a schematic illustration of an example embodiment of the pen device shown in FIG. 1B.

FIG. 1D shows a schematic illustration of an example embodiment of the pen device 10. The example shown in FIG. 1D illustrates the structural arrangement and interaction of the example modular units and mechanisms depicted in FIG. 1B for various operations of the pen device 10. As shown in FIG. 1D, the pen device 10 includes a mechanism to actuate a force to cause a displacement of a piston which resides within a medicament vial or cartridge 85. The displacement of the piston of the medicament vial 85 forces a volume of the medicament (that is proportional to the displacement of the piston) out of the vial 85, e.g., allowing it to be injected into a patient. The vial 85 is held within a medicament housing 25 of the pen device 10. The medicament housing 25 attaches to a main body housing 15 of the pen device 10, which includes a dose setting and dispensing mechanism and electronics unit of the pen device 10. In some embodiments, for example, the medicament housing 25 and the main body housing 15 may be a singular housing structure. The medicament housing 25 is structured to include a chamber to hold and/or encase the medicament vial 85 within the housing 25 of the pen device 10. The pen device 10 can also include a detachable pen cap (not shown) to cover an end of the pen device 10 that exposes a needle assembly (not shown) of the pen device 10 to disburse the medicine out of the pen device 10 when dispensed from the vial 85. The pen device 10 can include a vial spring 35, which provides a force on a screw retractor 55 to push the medicament vial 85 into the medicament housing 25 to ensure good dose accuracy. The pen device 10 includes a dose knob 20 attached to or included as part of the housing 15, where the dose knob is coupled to the housing by a non-self-locking thread 60. In some embodiments, for example, an electronics housing 30 may reside within the dose knob 20, in which the electronics housing 30 contains the electronics unit of the pen device 10. The dose setting mechanism includes a dose knob 20. When the dose knob 20 is rotated into or out of the housing 15 to adjust the dose, the electronics housing 30 does not turn. However, when translational or axial force is placed to the dose button 65 (e.g., in which resides the electronics housing), a catch structure component is engaged to lock the electronics housing 30 and dose knob 20 together, forcing them to rotate together as the pair travel back into the housing 15 upon actuation of the dose dispensing mechanism to apply force to the dose knob 20 to cause dispensing of the set dose. The rotation of the dose knob 20, e.g., which can be via the electronics housing 30, rotates a shaft 50 (e.g., which can be configured as a bi-directional clutch shaft). The shaft 50 in turn rotates a dose screw 70 which rides within a nut 75 which is fixed to the housing 15. This rotation causes the dose screw 70 to extend out of the housing 15 causing an injection of medicament. In some embodiments, for example, the dose dispensing mechanism can include a friction-causing structure 80, e.g., which can be coupled to the exemplary bi-directional clutch shaft 50 to present a frictionous surface (i.e., a surface that provides friction) to make contact with the nut 75 or housing body 15 or other internal structure of the dose dispensing mechanism, which acts from the bi-directional clutch shaft 50 to the housing 15 or nut 75 to prevent rotation of the shaft 50 while the dose setting mechanism is being adjusted via turning of the dose knob 20, but also allowing the friction to be overcome during the dose dispensing operation. In addition, by overcoming friction in the opposite direction the dose screw 70 may be driven back into the housing 15 and prepared for a new cartridge of medicament to be loaded. In some embodiments, for example, the pen device 10 includes a screw retractor component 55 that is axially fixed to the housing but rotationally free. The screw retractor component 55 is operable to be bent in to "grab" the non-circular cross section of the dose screw 70 allowing it to be rotated relative to the housing 15 and driven back into the housing 15. In some implementations, for example, the components of the pen device 10 could be manufactured by injection molding, machining or other similar process. In embodiments including the bi-directional clutch shaft, for example, the pen device 10 is capable of allowing retraction of the lead screw, and repeatability of operation of the dose dispensing mechanism.

In some embodiments, the sensor unit of the pen device 10 includes a rotational encoder, for example, between the dose knob 20 (e.g., which can be coupled to the jack screw) and the housing 15, and in electrical communication with the electronics unit contained in the electronics housing 30. The encoder is included in a sensor unit to determine the quantity of the dose set by the dose setting mechanism, and/or, the quantity of the dose dispensed by the dose dispensing mechanism. In some implementations, for example, the encoder can be configured in the pen device 10 to determine the dispensed dose by detecting rotation of the lead screw which is correlated with displacement of the pusher foot which is correlated with displacement of the receiving plunger in the vial 85, which in turn is correlated with dispensed insulin. In some embodiments, for example, the encoder can include two flat plates with contacts in between them. The plates are aligned perpendicular to the axis of the device. For one plate, a contact plate 40 is rotationally fixed to the jack screw, e.g., which can be via the electronics housing 30; and for the other plate, a code wheel 45 is rotationally fixed to the housing 15. In implementations, for example, when relative motion occurs between these two plates during dosing, the relative motion is measured and transmitted to the data processing and communications unit for processing, storage and/or transmission to the companion device 5.

In some embodiments of the pen device 10, for example, the dose setting and dispensing mechanism may include a mechanism in which the dose screw 70 is comprised of an elongate nut which screws in and out of the housing to provide dosing. The nut component in the previous described embodiment (e.g., nut 75) can include a separate screw structure; whereas in this embodiment of the dose screw, the nut component is part of the dose screw including exterior threads and is coupled to the housing 15. When the exemplary bi-directional clutch shaft 50 provides rotation, it operates on the jack screw, e.g., in which the dosing nut in this case threading it out of the housing.

Example embodiments and implementations of the disclosed intelligent medicine administering system for providing enhanced medicine dose recommendations for patient health management, including a medicine injection device (e.g., pen device) in communication with a companion device, are described herein. Some examples of features of an intelligent medicine administering system described herein can be used with the example devices, systems, and/or methods described in U.S. Pat. No. 9,672,328 B2, titled "Medicine Administering System Including Injection Pen and Companion Device," the entire content of which is incorporated by reference in this patent document.

While the disclosed embodiments described herein are primarily based on diabetes management systems and methods involving insulin pen and glucose monitoring devices to facilitate understanding of the underlying concepts, it is understood that the disclosed embodiments can also include treatment of other health conditions using other medications by the pen device and/or monitoring of other analytes by sensor devices.

Health Data Management Reporting and Decision Support Modules

In some aspects, the intelligent medicament delivery system 100 includes a report generator, an adaptive dose calculator and decision support modules to determine and recommend a time- and circumstance-relevant dose of a medicine (e.g., insulin) for the patient, and in some implementations, to provide control over the pen device 10 to set the dose. In some example implementations, a time- and circumstance-relevant dose of insulin is determined by the system 100 (e.g., by the app on the companion device 5 and/or on the pen device 10) based real-time analysis of retrospective and/or predictive information of glucose levels, e.g., provided by the example glucose sensor device 50 such as a CGM or smart blood glucose meter (e.g., smart BGM); information of insulin data including insulin dose data and insulin on board (IOB) data, e.g., provided by the pen device 10 and/or estimated by the app; and additional health data and/or contextual data including food intake, activity, location, and other user contextual circumstances associated with past, present and predictive future context of the user. In some examples, the IOB data can additionally or alternatively be provided by an insulin pump being used by the patient user, e.g., as some diabetic patient users may choose to alternate insulin pump use with an insulin pen for a time being and/or use an insulin pen as a supplement medication delivery device to the insulin pump.

The system 100 is configured to process the medicine data and health data, which includes analyte level values, and/or contextual data (e.g., food, activity, location, etc.) received from one or more software applications on the companion device 5 to produce a report that presents the medicine data, the analyte data and/or the contextual data in a manner illustrative of their relationship to each other. The report, produced by the system 100, is displayable on a display of the companion device 5, e.g., on a user interface of the app and/or as a report file, such as a PDF file, e.g., downloadable and/or displayable on a display of the companion device 5 or other computing device and/or printable via a printer. In example implementations described herein, the report presents the insulin data, the glucose data, and carbohydrate consumption (carb) data. The produced report includes a formatted data set of the insulin data, glucose data, and carbohydrate data organized on one or more [e.g., insulin, glucose, carb] value-time data plots with particular spatial arrangements of the data, from which the report data set can be further analyzed to interrogate statistical relationships of the temporally-relevant data presented on the value-time data plots. The system 100 is configured to re-process the produced report to retrospectively and/or predictively determine if dose calculator parameter adjustments are presently warranted based on analyzed relationships from the data produced in the report.

In the case of insulin as the medicine, for example, the system 100 can implement retrospective and predictive algorithms that can evaluate basal insulin efficacy by analyzing overnight glucose levels (i.e., overnight time period refers to a time period with no meals, e.g., 6 hours) and identify if there is a glucose steady-state or if there is glucose fluctuation or trend in a certain direction. For example, if a glucose steady state is determined, then the system 100 may not implement an insulin dose calculation adjustment method including a titration protocol; whereas, if a glucose fluctuation or trend in a certain direction is determined, then the system 100 may automatically or semi-automatically implement the insulin dose calculation adjustment method (e.g., a titration protocol) and adjust/update parameters associated with basal dosing, accordingly.

An example of the titration protocol for a basal insulin dose adjustment (i.e., dosing prior to a period without food intake) can include (a) titrating a fixed amount per a fixed period (1 U/day) until glucose levels are stable and/or until A1C levels (or average glucose values) are as desired; or (b) titrating a variable amount per a fixed period (e.g., +1 U per 50 mg/dL above target every 3 days). The example titration protocols can include safety features to halt titration or reverse titration based upon one or more of the following, for example: (a) if hypoglycemic episodes exceed a fixed rate (e.g., 2 per week), or (b) glucose levels are falling during time periods with no meals or (c) severe hypoglycemia is observed during time periods with no meals. An example method for adjusting an insulin dose calculation using a basal titration protocol is described in connection with the diagram shown in FIG. 5.

The algorithm can also include a module which determines if therapy intensification is recommended (e.g., adding basal insulin to oral only patients, or adding bolus insulin to basal only users, etc.). The protocol can use one or more factors for intensification of therapy, which can include (a) current therapy regimen, (b) A1C or average glucose, (c) post meal glucose rise, and/or (d) glucose stability during non-meal periods.

An example of the titration protocol for a bolus insulin dose adjustment (i.e., dosing based on food intake) can include (a) receiving an updated glucose value corresponding to the current glucose value; (b) determining whether the updated glucose value is within a range associated with the target glucose value; (c) when it is determined that the updated analyte value is above the range after one or more carb intake events (e.g., meals, snacks, etc.), then (c-1) re-calculating a second titration dose according to the titration protocol, and (c-2) displaying the second titration dose on the display device; and (d) repeating (a), (b), (c) until the current analyte level reaches the target analyte level acceptable well after meals. An example method for adjusting an insulin dose calculation using a fixed dose bolus titration protocol is described in connection with the diagram shown in FIG. 6.

Example implementations of the retrospective and predictive algorithms of the system 100 for evaluating basal and/or bolus dose insulin efficacy, with respect to the patient's glucose levels in conjunction with contextual factors, and adaptively determining certain parameters for adjustment can include the following.

In some implementations, for example, insulin action time can be adjusted by the algorithm by determining when glucose levels stabilize after each insulin dose. The algorithm can filter doses from the analysis by scoring the quality of the dose events and the glucose data available after the event. As an example, a dose where a second dose was given within 6 hours of the first dose could be excluded as it affects glucose stability of the first dose. After filtering dose events, the algorithm can determine the insulin action time by taking the average of the events or other statistical derivation such as $90^{th}$ percentile action time from the data set. An example method for adjusting an insulin action time is described in connection with the diagram shown in FIG. 7.

In some implementations, for example, insulin-to-carb ratio can be adjusted by the algorithm by determining the change in glucose level from the start of the dose to the level after the dose has been used as defined by the dose time plus the insulin action time. The algorithm can filter dose events from the analysis by scoring the quality of the dose events, carbohydrate intake and the glucose data available after the event. As an example, a dose where a second dose was given within 6 hours of the first dose could be excluded as it affects glucose stability of the first dose. After filtering dose events, the algorithm can determine the insulin-to-carb ratio by taking the average glucose change in the data set or other statistical derivation such as $90^{th}$ percentile, and increasing the insulin-to-carb ratio when the glucose falls, or decreasing when glucose rises. The adjustment can be performed by (a) adjusting a fixed amount per a fixed period (e.g., 1 g/U per day) until glucose levels are stable or (b) adjusting a variable amount per a fixed period (e.g., 1 g/U per 10 mg/dL change). An example method for adjusting an insulin-to-carb ratio is described in connection with the diagram shown in FIG. 8.

In some implementations, for example, insulin sensitivity factor can be adjusted by the algorithm by determining the distance from glucose target after glucose correction doses have completed their action as defined by the dose time plus the insulin action time. The algorithm can filter dose events from the analysis by scoring the quality of the dose events, and the glucose data available after the event. As an example, a dose where a second dose was given or a meal was consumed within the insulin duration after of the first dose could be excluded as it affects glucose stability of the first dose. After filtering dose events, the algorithm can determine the insulin sensitivity factor by taking the average glucose amount from target in the data set or other statistical derivation such as $90^{th}$ percentile, and increasing the insulin sensitivity factor when the glucose is below target, or decreasing when glucose is above target. The adjustment can be performed by (a) adjusting a fixed amount per a fixed period (e.g., 1 mg/dL/U per day) until glucose levels are stable or (b) adjusting a variable amount per a fixed period (e.g., 1 mg/dL/U per times the average distance from target). An example method for adjusting an insulin sensitivity factor is described in connection with the diagram shown in FIG. 9.

For fixed dose users, who take the same dose for every type of meal (e.g., 4 U with breakfast, 6 U with lunch, etc.), for example, the algorithm can determine the most optimal dose size without introducing dangerous or frequent hypoglycemia according the same method as in the insulin-to-carb ratio adjustment.

For fixed dose users, for example, the algorithm can add glucose correction to the fixed dose when glucose values are available at time of recommendation.

For users not skilled in carbohydrate estimation, the interface can allow for meal estimation, where users can select small, medium or large meal (e.g., large breakfast). The algorithm can subset the history of dose events by time of day (e.g., breakfast doses), and by size (e.g., large breakfasts) and perform an analysis similar to fixed dose adjustment to determine the optimal dose size for each subset (e.g., optimal large breakfast dose amount).

For meal estimators, for example, the algorithm can add glucose correction to the estimated meal dose when glucose values are available at time of recommendation.

The algorithm can determine the optimal dose for a common meal (e.g., a hamburger, such as a menu item by a restaurant) by sub setting the history of doses which correspond to that meal. For example, if the specifics of a meal are not known, the algorithm can subset dose events by GPS location, and scoring probability the user was at a specific restaurant by using reverse location lookup. The subset can then be filtered for outliers and results analyzed and a statistical optimal dose determined (e.g., average, $75^{th}$ percentile, etc.).

The algorithm can subdivide data sets by time of day and determine if different settings by time of day are more optimal.

Figure 2:
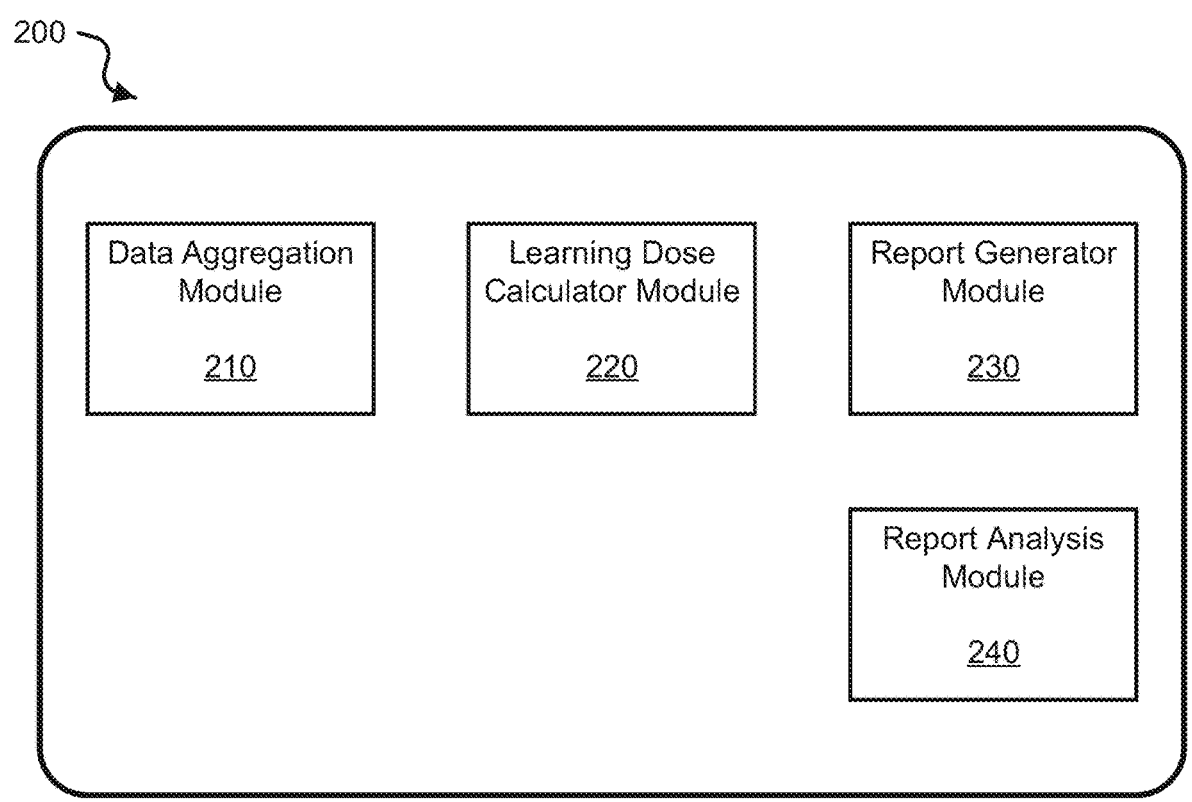
FIG. 2 shows a diagram of an example software architecture of data processing modules in accordance with some example embodiments of the intelligent medicine administering system.

FIG. 2 shows a diagram of an example software architecture of data processing modules in some example embodiments of the app of the intelligent medicine administrating system 100. The diagram depicts an example software architecture 200 for processing health data and contextual data obtained by the app on the companion device 5 from the pen device 10, from the sensor device 50, and/or from other devices of the patient user and/or apps on the companion device 5. In some embodiments, the software architecture 200 is embodied as part of the app resident on the companion device 5. Similarly, in some embodiments, for example, the software architecture 200 can be embodied as part of a data processing system in the cloud (e.g., resident on one or more cloud computers). In some embodiments, the software architecture 200 is embodied as part of both the software app on the companion device 5 and the data processing system in the cloud, in which some or all of the modules of the software architecture 200 are shared or divided among the app on the companion device 5 and the data processing system in the cloud.

As shown in FIG. 2, the software architecture 200 includes a data aggregator module 210 configured to obtain the health data from a device, such as the pen device 10, sensor device 50, and/or other devices or apps in communication with the companion device 5. The software architecture 200 includes a learning dose calculator module 220 to adaptively and autonomously calculate a dose of the medicine associated with dose injections from the pen device 10 based on time-relevant and context or circumstances-relevant data specific to the patient user of the pen device 10. The software architecture 200 includes a report generator module 230 to process data associated with the health data, which includes analyte data and medicine dose data, and contextual data including food intake, activity, and other contextual data for producing a report illustrative of a relationship between the data. In some implementations of the system 100, the learning dose calculator module 220, the report generator module 230, and/or the report analysis module 240 receive data from the data aggregation module 210 to be processed by the respective modules 220, 230 and/or 240.

The example modules of the software architecture 200 can be organized to provide data to one another in various ways, including directly (e.g., module-to-module) and/or indirectly (e.g., via an intermediary module), based on a periodic, an intermittent, and/or a per-request basis. It is noted that while the app is described as resident on the companion device 5, it is understood that some or all of the software modules of the app may be resident on the pen device 10 or in a centralized networked computer server, e.g., the cloud, and may be distributed across multiple locations.

In some example embodiments, the learning dose calculator module 220 is configured to receive and process health data and user contextual data to calculate a time-relevant and circumstance-relevant dose amount that the system recommends to the patient to dose. For example, the health data can include (i) information pertaining to the medicine to dose (e.g., type of medicine in the pen device 10 to dose, such as type of insulin; previous amount or amounts dosed, such as last dose or a historical dose; and/or other medicines used by the patient), (ii) information pertaining to a measured analyte (e.g., glucose value, including present glucose values, present glucose trend, and/or historical glucose values and trends), and (iii) other contextual information including additional health-related information, such as user's heart rate, blood pressure, menstrual cycle, other medicinal data, etc. and/or food intake, activity, location, or other user circumstance-related information. For example, the contextual data can include food intake (e.g., amount of carbs and/or total calories), physical activity (e.g., timing of activity or exercise, associated calories burned, etc.), the patient's location (e.g., at a restaurant, gym, home, etc.), the patient's mental state, and other data related to the patient's behavior and lifestyle. The learning dose calculator module 220 can receive data from one or more devices of the patient user, such as the pen device 10, an analyte sensor device 50 such as a glucose meter (e.g., continuous glucose monitor (CGM) device or single measurement blood glucose meter (SMBG) device), and/or activity monitors (e.g., activity or exercise watch or smartwatch, pedometer, and the like). The learning dose calculator module 220 can receive data from other software applications resident on the companion device 5, e.g., such as health aggregation apps like Apple HealthKit and/or Google Fit, and the like. The learning dose calculator module 220 processes the medicine, analyte and contextual information to produce time- and circumstance-relevant dose data for recommending a certain dose of the medicine for the user at a particular time.

In some example embodiments, the report generator module 230 is configured to produce a report from the aggregated data that presents the medicine data, the analyte data and/or the contextual data in a manner illustrative of their relationship to each other. The report generator module 230 can include one or more report template constructs that the report generator module 230 uses to format the data in accordance with certain spatial arrangements of the medicine, analyte and/or contextual data based on the magnitude and temporal values of each piece of data for the data categories. The formatted data of the produced report is provided to the report analysis module 240.

Figure 3:
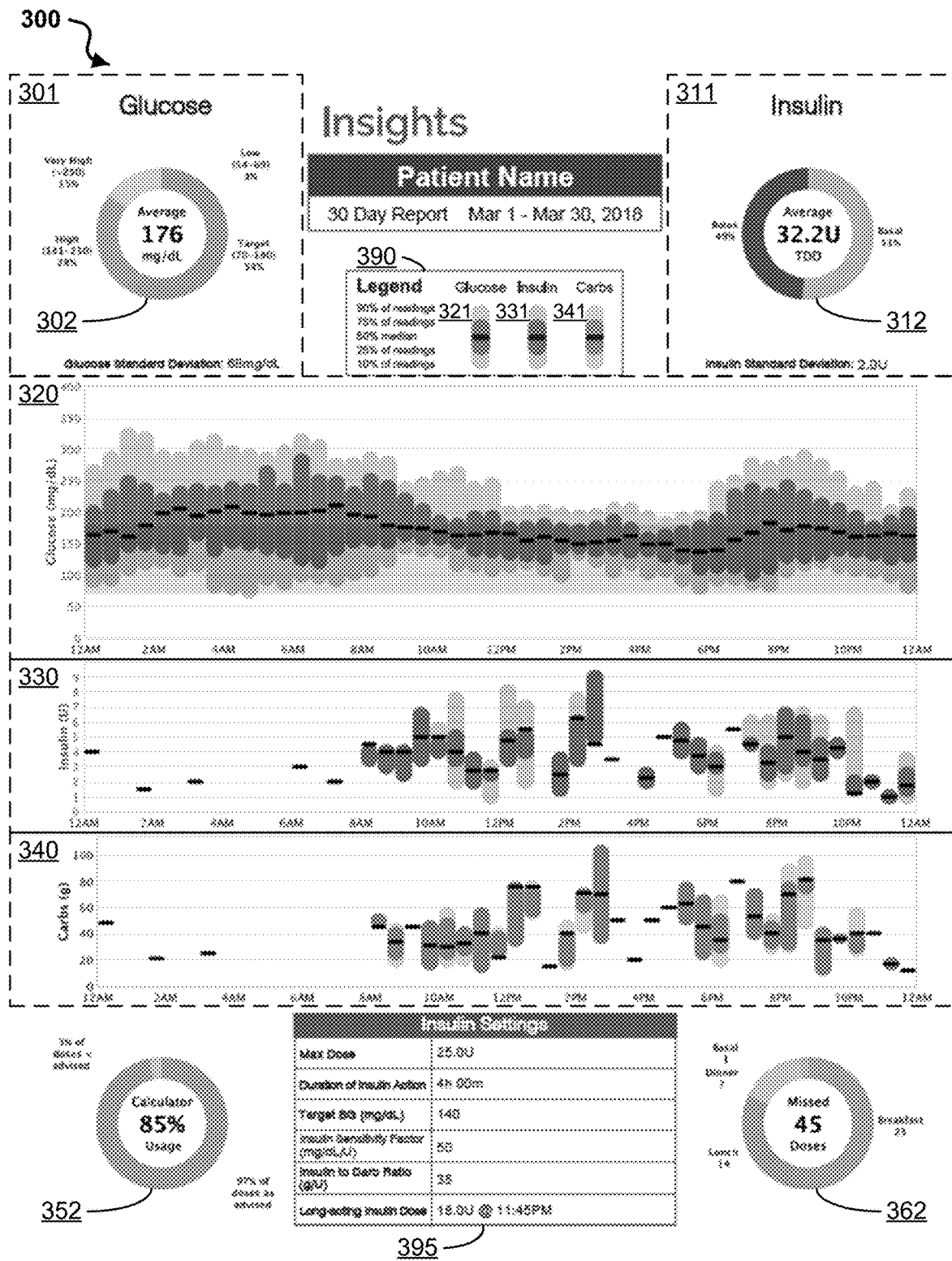
FIGS. 3 and 4 show illustrative diagrams of example embodiments of a report produced by the intelligent medicine administering system.

FIG. 3 shows an illustrative diagram of an example report 300 produced by the report generator module 230. The report 300 includes a plurality of sections that provide certain data associated with the medicine data (e.g., insulin data), analyte data (e.g., glucose data) and contextual data (e.g., carbohydrate data) on the report. In the example shown in FIG. 3, the report 300 includes a glucose data section in the top-left region of the report illustrated in dashed-box area 301, e.g., depicting a graphical feature 302 (e.g., donut plot) that indicates glucose levels averaged over a time period associated with data in the report, e.g., such as a 24 hour period, including a total average, and % time spent in predetermined analyte level regions (such as low, target, high and very high). In the example donut plot 302, the average level of glucose is featured in the middle of the donut plot 302. The report 300 includes an inulin data section in the top-right region of the report illustrated in dashed-box area 311, e.g., depicting a graphical feature 312 (e.g., donut plot) that indicates insulin dose information averaged over the time period, such as averaged units of insulin administered (e.g., total daily dose (TDD)) and % amount of basal vs. bolus insulin administered. In the example donut plot 312, the average units of insulin administered is featured in the middle of the donut plot 312.

The report 300 includes value-time data plots for glucose (mg/dL) illustrated in dashed-box area 320, insulin (units administered) illustrated in dashed-box area 330, and carbs (g) illustrated in dashed-box area 340, respectively, which are positioned in the middle region of the report 300. The report 300 depicts the glucose, insulin and carb data in the value-time data plots each using a data indicator graphic that presents a 50% median value and two levels of higher and lower values from the 50% median value, e.g., depicted as a 90% of median reading and a 75% of median reading for the higher values, and a 10% of median reading and a 25% of median reading for the lower values. In the legend of the report 300, shown in the upper-center region of the report and labeled 390, an example of the data indicator graphic 321, 331 and 341 for glucose data, insulin data and carbs data, respectively, which illustrates the 50% median value and example regions of the two levels of higher and lower values. In the data plots shown in box areas 320, 330 and 340, the glucose, insulin and carb data indicator graphics 321, 331 and 341 are presented on the value-time data plots at the particular time that they are associated with during the presented time period. In some embodiments, the report 300 aligns the time axes of the glucose, insulin and carbs value-time data plots such that the glucose, insulin and carb data indicator graphics 321, 331 and 341 are temporally aligned, which allows a patient user to easily visualize the effects of each of glucose, insulin and carbs on each other, and thereby the patient's overall diabetes management at each discrete time value.

In some embodiments, the report 300 can include the patient user's medicine settings (e.g., insulin settings), which can be presented on the graphical user interface display in a table (like table 395 for insulin settings) in a lower region of the report 300. In the example of FIG. 3, the medicine settings table 395 includes a max dose setting, a duration of medicine action time setting, a target analyte setting, and/or other settings.

In some embodiments, the report 300 can include additional graphical features (e.g., donut plots) associated with the dose calculator feature of the app on the companion device 5. For example, as shown in the example of FIG. 3, the report 300 includes a dose calculator usage donut plot 352 depicting an averaged % of instances a user may use or at least receive a recommended dose from the dose calculator, and a % of administered doses that were at, above or below the recommended dose amount provided by the dose calculator. Also, for example, the report 300 includes a missed doses donut plot 362 depicting the total doses missed (e.g., from those recommended by the dose calculator), and a breakdown of what/when the missed doses are associated with.

The report 300 provides an optimal format that allows multiple types of users, such as patients, advanced caregivers (e.g., physician, nurse, etc.) and novice caregivers (e.g., family member, friend, etc.), to concisely review the graphically formatted and displayed medicine, analyte, and contextual data so that intelligent and appropriate decisions can be promptly made. For example, the report 300 uniquely displays interrelated health data on a single plot, such as levels of a medicine for treating a health condition (e.g., insulin for treating diabetes), a monitored analyte associated with the health condition (e.g., glucose), and contextual information associated with management of the health condition (e.g., carbs). In the example of FIG. 3, the report 300 scales the insulin, glucose, and carbs proportionately on the plot. For example, the interrelated health data (e.g., insulin, glucose and carbs) are scaled so that carbs and insulin have a vertical height equal to the glucose impact that each of these would have upon glucose—this can be based on the patient user's insulin-to-carb ratio and insulin sensitivity factor. Also for example, the report generation module 230 can format the data graphical indicators 321, 331 and 341 of the report 300 to limit a maximum height so large amounts that would otherwise extend off the page are still presented on the plot and/or to project a viewable height for a data of a minimum value otherwise unviewable. Furthermore, the report 300 can display missed doses in a time period in a manner that is accountable by the learning dose calculator 220 so that the appropriate dose recommendation can be made, e.g., such as in the case of a missed dose that would not need to be 'counted' if the patient didn't eat a meal or undertook other behavior such that the patient's glucose levels stayed within the target range.

The report 300 provides a structured format such that the system 100 can efficiently analyze organized data based on a reduced data set and provide data feedback to (i) the learning dose calculator module 220 to recommend a dose and/or alter dose settings or parameters and/or (ii) the report analysis module 240 to dynamically modify the display or restructure the report 300. In some implementations, the report 300 allows the system 100 to automatically analyze the patient user's health condition management situation and behavior and take action, e.g., such as adjust medicine dose settings or parameters and/or alert the patient user. In an illustrative example of the system 100 used in diabetes management, missed basal insulin dose(s) can be determined by the system 100 looking for a dose in the dose history using the report 300, e.g., within a time period around a user-configured scheduled dose time (e.g., +/−3 hours around 10 PM dose). In some implementations, for example, missed basal insulin dose(s) can be determined by the system 100 by automatically assessing glucose stability in time periods without meals and determining if the glucose rate of change differs from the time where the dose was given. In some implementations, missed meal doses can be determined in the same manner, e.g., either time based (e.g., breakfast dose logged between 7 AM and 9 AM) or by determining meal events by observing glucose rises in the formatted report 300.

For example, in cases where the user's glucose level (e.g., blood glucose (BG)) is within a defined target range at a defined time or time period after a suspected missed dose, the system 100 can identify and indicate that the patient user had proper BG control throughout this period and did not require an insulin dose, and the dose calculator module 220 will not count this instance as a missed dose. Also, for example, in cases where the dose calculator module 220 recommends taking no insulin, even at a known dose time or meal time, the system 100 can account for this instance by not counting this as a missed dose since no dose was recommended. In cases where the dose calculator module 220 was not operated by the system 100 (e.g., because the user did not interact with the app), but a calculation performed by the system 100 indicates that a dose would not have been recommended at the time of a known dose or meal, this instance would not be counted as a missed dose. In cases where a set meal time passes with no dose taken, the app may prompt the user to manually indicate whether they did not actually eat, or if they did in fact miss the dose. If the user indicates that they did not eat, this instance will not be counted as a missed dose.

In some embodiments, the report 300 may include a graphical representation of missed doses at the time on the graph when the dose should have been taken, e.g., at the particular time points on the glucose value data plot 320 and/or insulin value data plot 330. For example, this may be shown as a symbol such as a red circle. In some embodiments of the report 300, the proper dose amount may also be displayed. For example, the proper dose amount can be calculated by a dose calculator calculation, e.g., the patient user's fixed dose amount, or based on carbs consumed at this time. Alternatively, the proper dose amount can be calculated by evaluating the ensuing glucose value a fixed time after the missed dose to determine the amount of insulin that would have brought it to target level. For example, if the user does not dose at a meal time, and the meal size is unknown but the user's BG was 250 mg/dL at two hours after the meal, then the insulin required to correct 250 mg/dL BG level to the target level or range can be calculated. In this example, the calculation is as follows: Dose=(BG−Target BG)/(Insulin Sensitivity Factor). If, for example, the target BG level was 120 mg/dL and Insulin Sensitivity Factor was 20 mg/dL/Unit for this patient user, then (in the case of the patient user's 250 mg/dL BG level) the user should have taken 6.5 Units of insulin (based on the calculation: (250−120)/20=6.5 U). In this example, at this meal time, a missed 6.5 U dose would be indicated graphically on the report 300.

Figure 4:
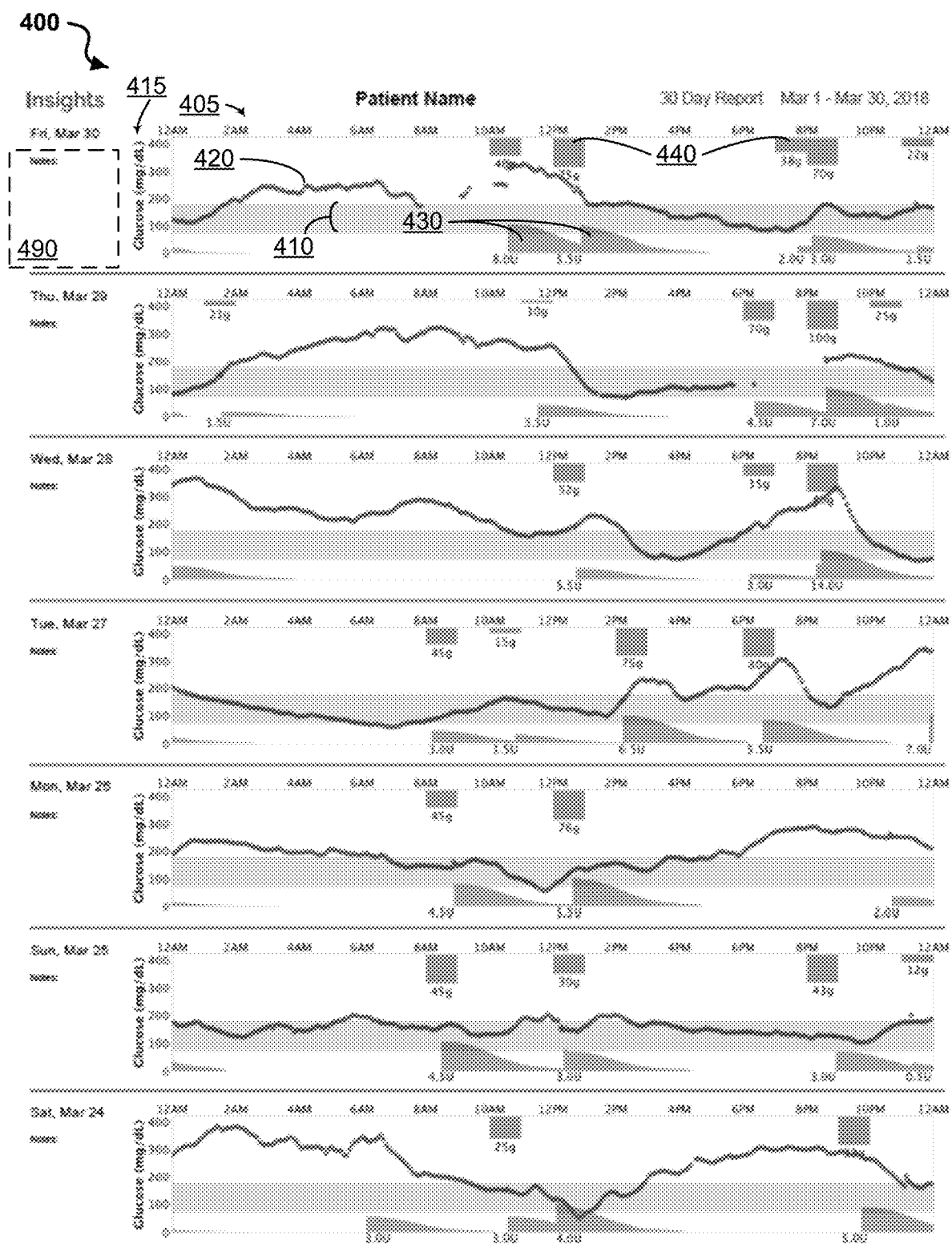

FIG. 4 shows an illustrative diagram of an example report 400 produced by the report generator module 230. The report 400 includes a series of value-time data plots over a time period (e.g., 24 hours, depicted by time axis 405) for a series of the time periods (e.g., several days, such as a week), which can be arranged in temporal order with time axis 405 aligned for each series of value-time data plots. In the example of FIG. 4, the report 400 includes a series of seven value-time data plots over a one-week period, e.g., shown as Saturday, Sunday . . . Friday, which are arranged from oldest data plot toward the bottom to newest toward the top of the report 400. The value-time data plots of the report 400 include the glucose level data (plot 420) presented over the time period with respect to the insulin dose data (plot 430) and carb intake data (plot 440) that are spatially arranged on the plot with respect to time and magnitude to the glucose plot 420. In some embodiments, the report 400 includes a target glucose region 410, which can be individually defined for each patient user of the system 100 (e.g., by the learning dose calculator 220 and/or by data input, via the app, by a caregiver or the patient user). In some embodiments, the report 400 can include a notes region 490 where notes by the patient user and/or caregiver can be displayed. In some implementations, for example, the app allows a user to dynamically enter notes after an initial generation of the report 400 is displayed, e.g., via a touch command by the user on the display to create an input box that allows the user to type or upload text, graphics or other input.

As shown in FIG. 4, glucose, insulin, and carbohydrate values are overlaid on the same plot, and all scaled proportionately to glucose. The range of the vertical axis 415 of the graph is set to a fixed glucose range, e.g., between 0 and 400 mg/dL in this example. This may be defined by the limits of the glucose monitor device (e.g., fingerstick blood glucose meter or CGM sensor) or by common glucose values for a patient, e.g., such as 40 mg/dL to 600 mg/dL. While a patient cannot achieve 0 mg/dL, for visual clarity the graph minimum may be set to 0, for a range such as 0 mg/dL to 400 mg/dL.

In the example shown in FIG. 4, the insulin data and the carb data are arranged to depict 'pulling' on the glucose data, e.g., such that a (bolus) insulin dose administration event 'pulls' glucose levels down in the proximate time of the dose, and a carbohydrate consumption event pulls glucose levels up in the proximate time of the carb intake. It is noted that, in some examples, the report generator module 230 produces a multipage report that includes the report 300 and the report 400 in a single report. For example, carbs are known to adjust a diabetes patient's blood glucose level upward by a calculatable amount, and insulin is known to adjust the patient's blood glucose level downward by a calculatable amount. As such, the report generation module 230 can scale both carbs and insulin data on the value-time data plot in report 400 according to their calculated effects on glucose level.

Insulin is related to blood glucose by the user's configured Insulin Sensitivity Factor (ISF). Units of insulin multiplied by ISF equals the expected glucose change. For example, if ISF is equal to 20 mg/dL/Unit, then a 2 unit dose of insulin would be expected to reduce glucose by 2×20=40 mg/dL. For this patient user, for example, a 2 unit dose would be scaled to the height of 40 mg/dL on the graph, at the time point associated with the insulin dosing event, in the report 400. Insulin is displayed along the bottom of the graph so that visually it "pulls" the glucose trend downward.

Carbohydrates are related to blood glucose by the user's configured ISF and Insulin-to-Carb Ratio (ICR). Grams of carbohydrates are divided by ICR to determine an equivalent insulin amount, and then, that is multiplied by ISF to determine the expected glucose change. For example, if ISF is equal to 20 mg/dL/Unit and ICR is equal to 10 gram/Unit, then a meal with 30 grams of carbohydrates would be expected to raise glucose by (30/10)×20=60 mg/dL. For this patient user, a 30 gram carb meal would be scaled to the height of 60 mg/dL, at the time point associated with the carbs consumption event, on the graph in the report 400. Carbs are displayed along the top of the graph so that visually they "pull" the glucose trend upward.

In some embodiments of the report 400, for visual clarity, the carb and insulin scaling may be limited so that small amounts are visible, and large amounts do not obscure other information on the graph or extend off the page. After the normal proportional scaling is applied, the vertical height is limited to a minimum height based on what is clearly visible in the report, e.g., 10 pixels or 10% of the overall graph height. Vertical height may also be limited to a maximum height based on what will not obscure other information or extend past the limit of the graph, e.g., 33% of the graph height or 90% of the graph height.

Yet, in some embodiments, rather than scaling all values to equivalent glucose level, the report generation module 230 may scale the values relative to the largest value for the period displayed in the graph. In this way, the largest carb or insulin value is scaled to a fixed height, e.g., 33% of the graph height, and all other values of the type are scaled proportionally to that. The minimum height limit is still enforced, setting small amounts to a fixed minimum height so they remain visible.

Yet, in some embodiments, the report generation module 230 may scale the values relative to the smallest value for the period displayed in the graph. In this way, the smallest carb or insulin value is scaled to a fixed height, e.g., 10% of the graph height, and all other values of the type are scaled proportionally to that. The maximum height limit is still enforced, setting large amounts to a fixed maximum height so they do not obscure other information or run beyond the limit of the graph.

In accordance with some example embodiments, the system 100 can be configured for tracking a dose of a medicine to a patient and generating a dynamic report (e.g., the report 300 and/or report 400), in which the system 100 includes the pen device 10 in communication with the companion device 5, where the companion device 5 and/or the pen device 10 include the software application (app) to cause the companion device 5 and/or the pen device 10 to determine a recommended dose based on medicine data (e.g., insulin data, including prior doses), health data, and contextual data associated with a patient user of the pen device 10. The health data includes analyte data (e.g., glucose data), and the contextual data includes nutrient data corresponding to a food (e.g., carbohydrates data), in which the app includes a data aggregator (e.g., dose aggregation module 210) configured to obtain the health data and the contextual data, a dose calculator (e.g., learning dose calculator module 220) configured to autonomously determine the recommended dose of the medicine, and a report generator (e.g., report generator module 230) configured to produce a dynamic report that is displayable on a display of the companion device 5 and/or the pen device 10 and that is illustrative of a relationship between the medicine data, the health data, and the contextual data. The report generator is configured to format the report to include the medicine data, analyte data, and nutrient data each represented by a graphical indicator plotted on a single graph such that the graphical indicators associated with the medicine data and the nutrient data are spatially aligned and sized with the graphical indicator associated with the analyte data based on (i) temporal information of the medicine data, the analyte data, and the nutrient data and (ii) a dynamic trend of the analyte data that determines a size of the graphical indicators associated with the medicine data and the nutrient data scaled to a rate of change of the dynamic trend. In some embodiments, the app includes a report analyzer (e.g., report analysis module 240) configured to analyze formatted data of the generated report to determine a statistical relationship of a temporally-relevant factor between the medicine data, analyte data, and nutrient data spatially arranged on the graph. In some embodiments, the dose calculator autonomously is configured to determine the recommended dose of the medicine based on an analysis of the generated report, e.g., including by the determined statistical relationship of the temporally-relevant factor In some embodiments, the dose calculator is configured to produce an output that includes executable code to cause the pen device 10 to actuate an operation including, but not limited to, automatically setting the dose of the medicine to a calculated medicine dose value and/or generating an alert indicative of a medicine dispensing event at the calculated medicine dose value.

In accordance with some example embodiments, the system 100 can be configured for determining a dose of a medicine to a patient and adaptively accounting for a missed dose, in which the system 100 includes the pen device 10 in communication with the companion device 5, where the companion device 5 and/or the pen device 10 include the software application (app) to cause the companion device 5 and/or the pen device 10 to determine a recommended dose based on medicine data (e.g., insulin data, including prior doses), health data, and contextual data associated with a patient user of the pen device 10. The health data includes analyte data (e.g., glucose data), and the contextual data includes nutrient data corresponding to a food (e.g., carbohydrates data), in which the app includes a data aggregator (e.g., dose aggregation module 210) configured to obtain the health data and the contextual data, a dose calculator (e.g., learning dose calculator module 220) configured to autonomously determine the recommended dose of the medicine, and a user interface generator (e.g., user interface generation module) configured to produce a user interface on a display of the companion device 5 and/or the pen device 10 that displays, on the produced user interface, the recommended dose. The dose calculator is configured to autonomously modify the determined recommended dose of the medicine when the determined recommended dose was not administered by the pen device 10 in a predetermined time period (e.g., within 5 minutes, 10 minutes, 1 hour, or other time period) from display of the recommended dose to qualify as a missed dose; and the user interface generator is configured to produce the user interface to include an indication of the missed dose. In some embodiments, the dose calculator is configured to determine when the missed dose occurred when an analyte level was within a target range at a time within or after the predetermined time period and thereby exclude the missed dose from calculation of the modified recommended dose. In some embodiments, the dose calculator is configured to determine when the missed dose occurred when no nutrient data was registered at a time within or after the predetermined time period and thereby exclude the missed dose from calculation of the modified recommended dose. In some embodiments, the dose calculator is configured to determine when the missed dose occurred based on the determined recommended dose being substantially zero and thereby exclude the missed dose from calculation of the modified recommended dose. In some embodiments, the dose calculator is configured to determine a missed dose when glucose levels rise to a predetermined level change within a time period after a meal time. In some embodiments, the user interface generator is configured to produce the user interface to include the indication of the missed dose as a symbol on a single graph that includes a plot of the analyte data and a graphical indicator associated with the medicine data. In some embodiments, the user interface generator is configured to produce the user interface to include the indication of the missed dose as an amount of the missed dose on a single graph that includes a plot of the analyte data and a graphical indicator associated with the medicine data. In some embodiments, the dose calculator is configured to calculate an amount of the missed dose based on a determined dose amount that would have corrected a resulting glucose level to a target level within a predetermined time period after the missed dose.

Dose Calculation and Parameter Adjustment

Dose calculation parameters can be adjusted automatically from the data in the report, as described in the examples below. It is noted, for example, that several days or instances can be used, such that a pattern is seen and that titration doesn't happen off of one incident.

For basal titration, for example, the report analysis module 240 can process the spatial arrangements of the glucose data with carb data, e.g., analyze the steadiness of the glucose data over time and relative differential of overnight glucose with no meals, to identify if the glucose levels after basal insulin dosing is steady (no titration needed), falling (titrate down) or rising (titrate up). The report analysis module 240 produces an analyzed data set that is provided to the learning dose calculator module 220.

In some implementations, the learning dose calculator module 220 can automatically update the basal dose and determine an updated output including a modified recommended basal insulin dose and/or reminders or alerts, e.g., in the long acting reminder, a generated reminder can recommend the user to take the updated recommended basal insulin dose the next time (e.g., next evening).

The report analysis module 240 can evaluate insulin action time (IAT) based on the formatted data in the produced report from the report generator module 230. For example, the report analysis module 240 can evaluate the report data by looking for periods where there was a correction dose and no meal or additional dose five or more hours after that dose. When the glucose stops changing, the insulin is used up and that is the action time. The report analysis module 240 can provide the evaluated IAT data to the learning dose calculator module 230.

The report analysis module 240 can evaluate insulin sensitivity factor (ISF) based on the formatted data in the produced report from the report generator module 230. For example, the report analysis module 240 can evaluate the report data by looking for correction only doses (no food) with no meal or additional dose five or more hours after that dose and measure the glucose drop from the dose time to the insulin action time, and calculate insulin sensitive factor as ISF=Glucose drop divided by correction dose. The report analysis module 240 can provide the evaluated ISF data to the learning dose calculator module 230.

After the ISF is configured, e.g., by the learning dose calculator module 220 based on the analysis of the report analysis module 240, the report analysis module 240 can evaluate insulin-to-carb ratio (ICR) based on the formatted data in the produced report from the report generator module 230. For example, the report analysis module 240 can evaluate the report data by looking for every meal where there is no dose or meal within the insulin action time after the dose (e.g., typically 5 hours). The report analysis module 240 can Calculate the ICR if carbs were correct, e.g., by: ICR=Carbs/(Dose amount+IOB amount−(starting glucose−ending glucose)/ISF). The report analysis module 240 can calculate the carbs in the meal if ICR was correct, e.g., by: Carbs=(Dose amount+IOB amount−(starting glucose−ending glucose)/ISF)*ICR. The report analysis module 240 can provide the evaluated ICR data to the learning dose calculator module 230. In implementations, for example, over a large data sets of doses and results, the report analysis module 240 can look at the variation of ICR and produce a regression line; such that, (1) if there is a high variability along the regression line, likely the user is not proficient around counting carbs, which can inform the learning dose calculator 230 to trigger meal estimation educational information to the user, and (2) if the variability is lower, update the ICR to the regression line, or some more conservative value based upon the titration aggressiveness setting.

The report analysis module 240 can evaluate target BG based on the formatted data in the produced report from the report generator module 230. For example, the report analysis module 240 can determine if the existing insulin dose parameters include parameter(s) that could be thought of as 'an aggressiveness setting(s)'. For example, if the user has a high target BG (e.g., above 100) with no hypos, the report analysis module 240 provides data that the learning dose calculator module 220 can use to determine one or more settings for gradually lower the target BG to achieve better A1C outcomes, and for stopping if hypos become more common than a define threshold. For example, if the user is having frequent hypos, the learning dose calculator module 220 can move the target BG up.

The report analysis module 240 can evaluate missed doses based on the formatted data in the produced report from the report generator module 230. For example, if there are many missed doses and the average glucose is high, the analyzed data that characterizes this set of results can allow the learning dose calculator module 220 to generate a recommendation to turn on missed dose alerts or turn them on for the user. Also, for example, the report analysis module 240 can confirm the time ranges for meals are correct for the user (of which, the app can prompt user to confirm). Notably, for example, if the time ranges for breakfast are not right, it can create false positive missed doses. The learning dose calculator module 220 can include an algorithm to look at BG patterns and/or dose timing patters and automatically configure meal time ranges. For example, a smarter missed dose algorithm can look at BG to see if they ate or not, and only report missed doses if there is a corresponding rise in glucose and no dose within a time range around the rise.

In various implementations, the learning dose calculator module 220 can process the analyzed data provided by the report analysis module 240 for various uses to formulate user-specific dose calculations. For example, if the patient has a high average glucose, frequently hypos or a lot of variability in glucose, recommend to the user to use the dose calculator or trigger educational content. For example, the learning dose calculator module 220 can correlate a success score of each dose (e.g., did they get to target after) to use of the dose calculator and override of the recommendation. If the patient has a high average glucose and they override the calculator lower than the recommendation frequently, the learning dose calculator module 220 can notify the user (e.g., generate an alert notification) that this may be the cause.

The report analysis module 240, in conjunction with the learning dose calculator module 220, can scrutinize the formatted data of the report produced by the report generator module 230 and modulate changes to the dose calculation settings and/or generate information for informing the user about prospective better outcomes. In addition to the examples above, the medicine, analyte and contextual data can be evaluated from the report to module change or provide information about the following example factors, including total daily dose, time of day, exercise, stress levels, and the like.

Total daily dose (TDD) factor: If the ratio is not close to 50/50 basal/bolus, the system 100 can ask the user if they are on a low carb diet or suggest adjusting the insulin regime closer to 50/50. Use basal titration above to assess correctness of basal amount.

Time of Day factor: If there are patterns of high or low glucose around a specific time of day, for instance early mornings, the system 100 can recommend enabling time of day settings and changing the target BG or other settings to avoid the issues for the time period.

Exercise factor: Insulin sensitive varies post exercise. The system 100 can allow the user to configure a set of insulin settings for post exercise and auto-enable the setting after the fitness tracker detects exercise for a period after exercise. Using the example algorithms described above, the system 100 can learn how long insulin sensitive is impacted for the user post exercise and use that time; and/or revert automatically to the standard settings after the exercise effect lessens.

Stress/Hormones factor(s): Similar to exercise factors, the system 100 can monitor insulin sensitivity related to stress and/or hormonal events, and trigger different settings for menstruation based upon a calendar, or when stress is detected, via heart rate, location (work), blood pressure or other signals. Revert settings once event passes.

Carbs on Board factor: Similar to insulin on board (e.g., daily chart on the example page 2 of the report in FIG. 4), the report generator 230 can plot carb on board as carbs remaining to be digested. This shows carbs raising potential glucose (i.e., pulling), e.g., with carbs plotted from top facing down to pull glucose upward. The report analysis module 240 can determine carb action time as time where glucose stops rising for each meal; carb action time varies per food type; learn carb action time for each type of food (e.g., pizza) to be used in future scenarios to adjust dose time or amount.

Predicted glucose factor: Plot difference of carb on board and insulin on board to give predicted glucose, plotted from current glucose forward.

The modules of the software architecture 200 (e.g., the data aggregator module 210, the learning dose calculator module 220, the report generator module 230 and/or the report analysis module 240) can obtain and process data from the pen device 10, the app associated with the pen device 10 (operating on the pen device 10 or the companion device 5) and/or other software applications operating on such devices, or other data resources to analyze and adjust insulin dose calculations or associated parameters.

Figure 5:
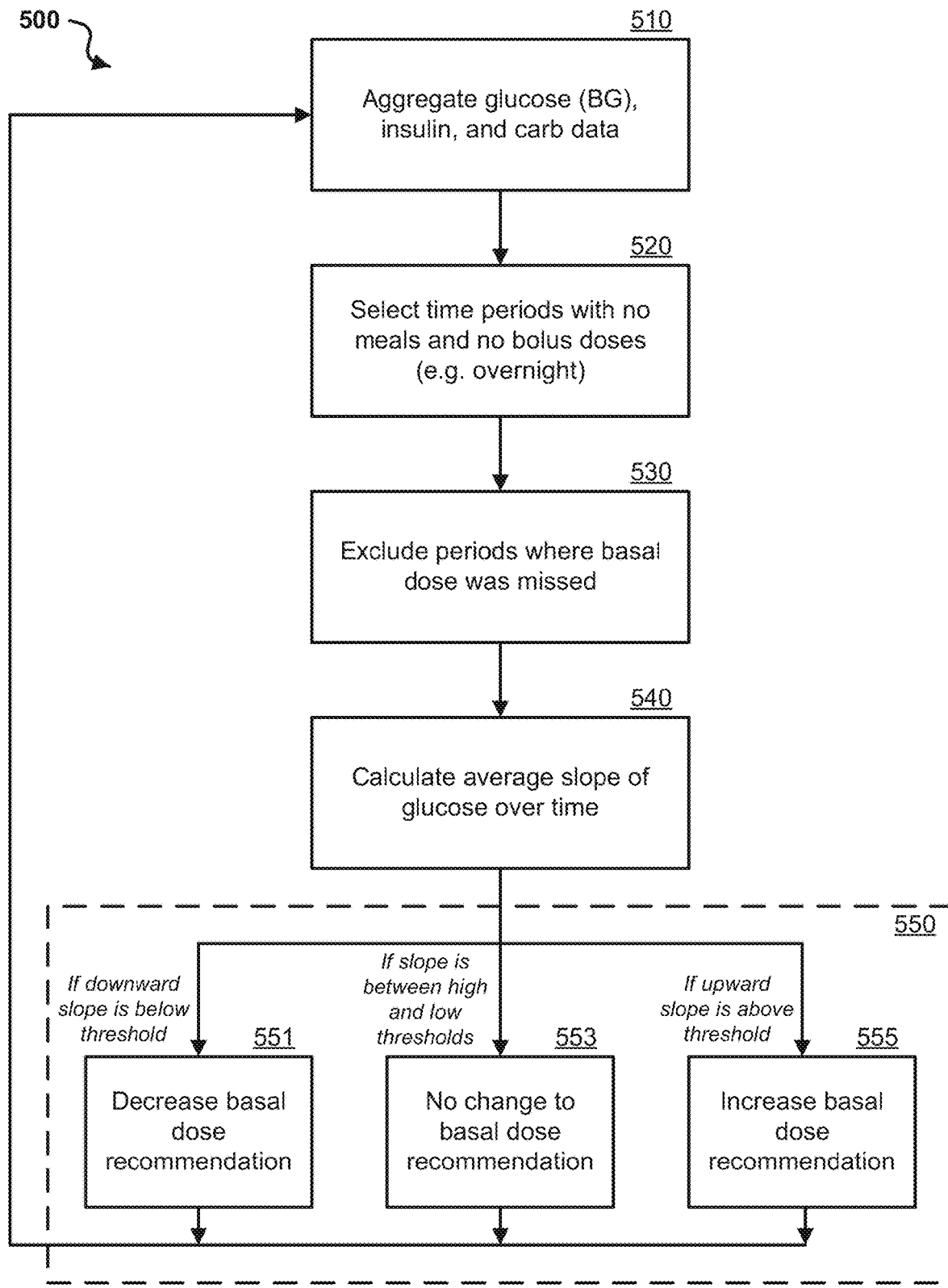
FIG. 5 shows a diagram of an example embodiment of a method for adjusting an insulin dose calculation using a basal titration protocol in accordance with the present technology.

FIG. 5 shows a diagram of an example method 500 for adjusting an insulin dose calculation using a basal titration protocol in accordance with the present technology. In various implementations, the method 500 can be implemented by the app associated with the pen device 10, which can include the modules of software architecture 200. The method 500 includes a process 510 to aggregate glucose data, insulin data, and carbohydrates data associated with a patient user. The method 500 includes a process 520 to select time period(s) with no meals and no bolus doses (e.g., such as overnight). The method 500 includes a process 530 to exclude periods where basal dose was missed by the patient user. The method 500 includes a process 540 to calculate the average slope of glucose levels over time. The method 500 includes a process 550 to adjust (or not adjust) a basal insulin dose recommendation based on the calculated average slope. In implementations where the slope is a downward slope that is below a threshold, a process 551 is implemented to generate a recommendation to decrease the basal dose. In implementations where the slope is between a high threshold and a low threshold, a process 553 is implemented to generate a recommendation to not change the basal dose. In implementations where the slope is an upward slope that is above a threshold, a process 555 is implemented to generate a recommendation to increase the basal dose. The determined basal insulin dose recommendation (adjustment or non-adjustment) data can be feedback to the process 510 in implementations of the method 500.

Figure 6:
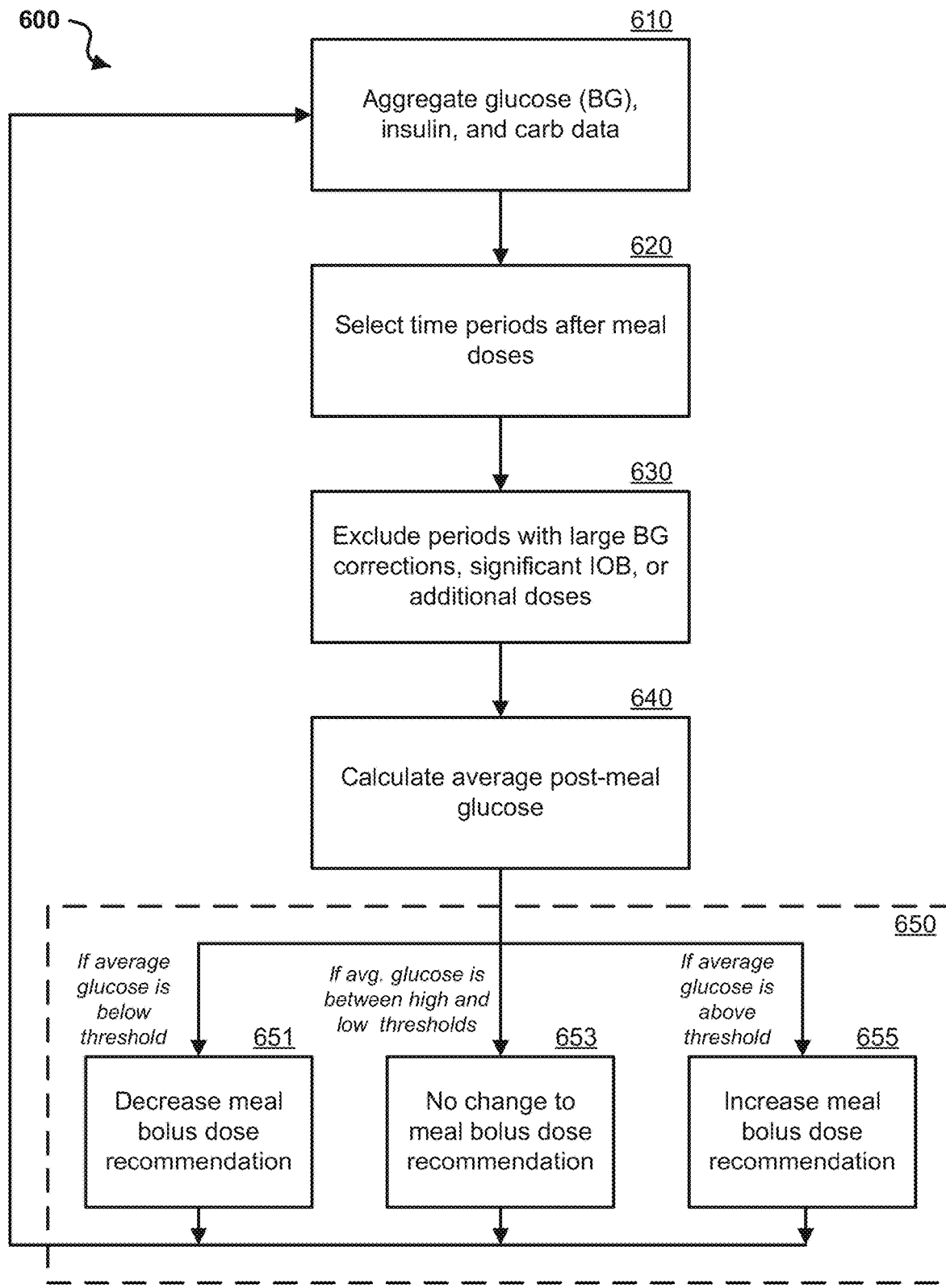
FIG. 6 shows a diagram of an example embodiment of a method for adjusting an insulin dose calculation using a fixed dose bolus titration protocol in accordance with the present technology.

FIG. 6 shows a diagram of an example method 600 for adjusting an insulin dose calculation using a fixed dose bolus titration protocol in accordance with the present technology. A fixed dose bolus titration procedure may typically be implemented periodically after a period of time on therapy (for example, several days to several months) so that the averaged results of the current therapy settings for the patient user can be evaluated and adjusted if necessary. In various implementations, the method 600 can be implemented by the app associated with the pen device 10, which can include the modules of software architecture 200. The method 600 includes a process 610 to aggregate glucose data, insulin data, and carbohydrates data associated with a patient user. The method 600 includes a process 620 to select time periods after doses administered temporally proximate to a meal (referred to as "meal doses"). The method 600 includes a process 630 to exclude period(s) with large BG corrections, significant insulin on board (IOB), or additional doses. Significant IOB can include an amount of insulin that would affect the patient user's glucose level by less than some amount (e.g., 10 mg/dL) as calculated based on the patient user's insulin sensitivity factor. In some examples, significant IOB can be 0.5 U or less. The method 600 includes a process 640 to calculate the average value of post-meal glucose levels over time (e.g., multiple meals). The method 600 includes a process 650 to adjust (or not adjust) a meal bolus insulin dose recommendation based on the calculated average. In implementations where the average glucose level is below a threshold, a process 651 is implemented to generate a recommendation to decrease the meal bolus dose. In implementations where the average glucose is between a high threshold and a low threshold, a process 653 is implemented to generate a recommendation to not change the meal bolus dose. In implementations where the average glucose is above a threshold, a process 655 is implemented to generate a recommendation to increase the meal bolus dose. The determined meal bolus dose recommendation (adjustment or non-adjustment) data can be feedback to the process 610 in implementations of the method 600.

Figure 7:
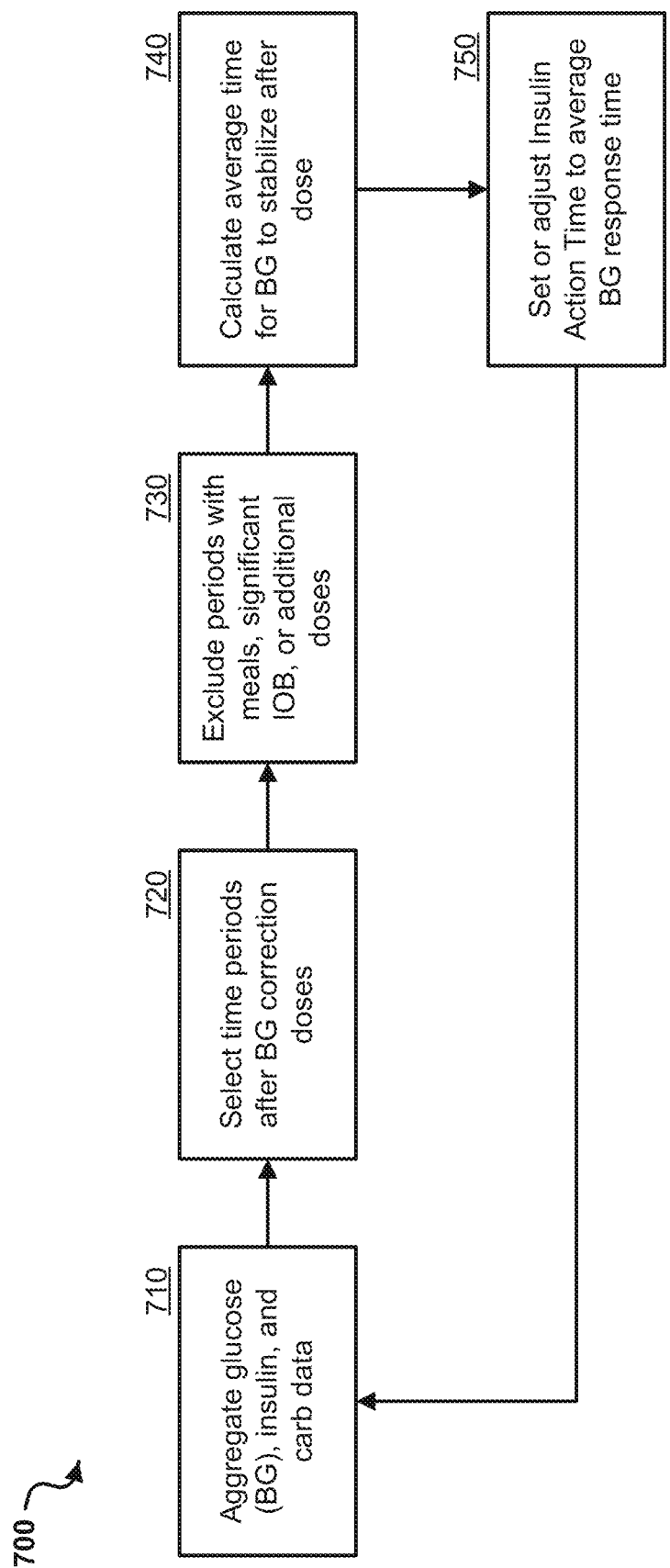
FIG. 7 shows a diagram of an example embodiment of a method for adjusting an insulin action time parameter in accordance with the present technology.

FIG. 7 shows a diagram of an example method 700 for adjusting an insulin action time parameter in accordance with the present technology. In various implementations, the method 700 can be implemented by the app associated with the pen device 10, which can include the modules of software architecture 200. The method 700 includes a process 710 to aggregate glucose data, insulin data, and carbohydrates data associated with a patient user. The method 700 includes a process 720 to select time period(s) after a glucose correction dose is administered. The method 700 includes a process 730 to exclude period(s) with large BG corrections, significant insulin on board (IOB) or additional doses. The method 700 includes a process 740 to calculate the average time for glucose level to stabilize after the dose. The method 700 includes a process 750 to set or adjust the insulin action time (IAT) to the average glucose response time, e.g., based on the value calculated in the process 740. The determined insulin action time data from the process 750 can be feedback to the process 710 in implementations of the method 700.

Figure 8:
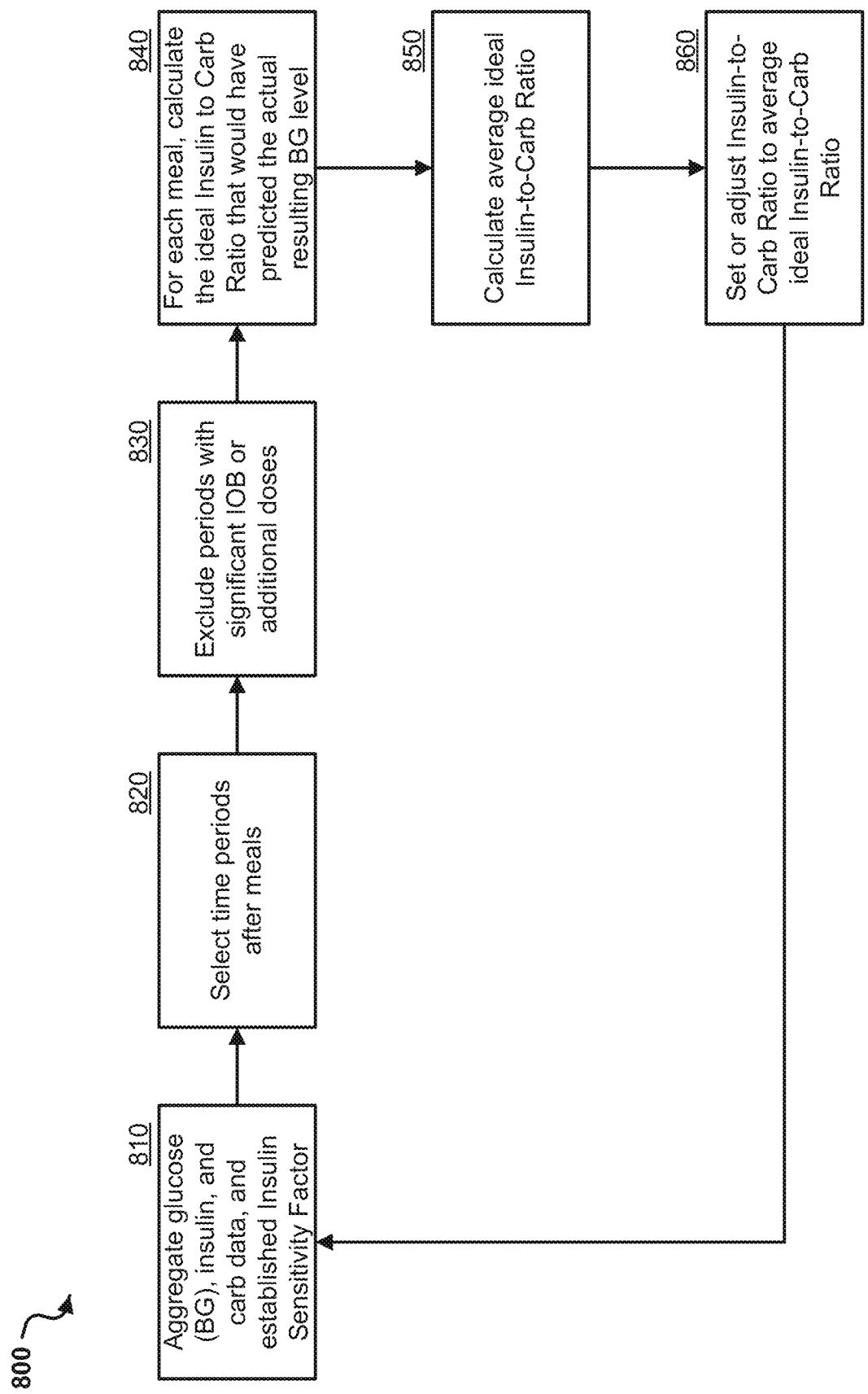
FIG. 8 shows a diagram of an example embodiment of a method for adjusting an insulin-to-carb ratio parameter in accordance with the present technology.

FIG. 8 shows a diagram of an example method 800 for adjusting an insulin-to-carb ratio parameter in accordance with the present technology. In various implementations, the method 800 can be implemented by the app associated with the pen device 10, which can include the modules of software architecture 200. The method 800 includes a process 810 to aggregate glucose data, insulin data, carbohydrates data, and established insulin sensitivity factor (ISF) data associated with a patient user. The method 800 includes a process 820 to select time period(s) after meal(s). The method 800 includes a process 830 to exclude period(s) with significant insulin on board (IOB) or additional doses. The method 800 includes a process 840 to calculate, for each meal, the ideal insulin-to-carb ratio (IICR) that would have predicted the actual resulting glucose level. The method 800 includes a process 850 to calculate the average ideal insulin-to-carb ratio (AIICR). The process 800 includes a process 860 to set or adjust the insulin-to-carb ratio (ICR) to the average ideal insulin-to-carb ratio (AIICR), e.g., based on the value calculated in the process 850. The determined ICR data from the process 860 can be feedback to the process 810 in implementations of the method 800.

Figure 9:
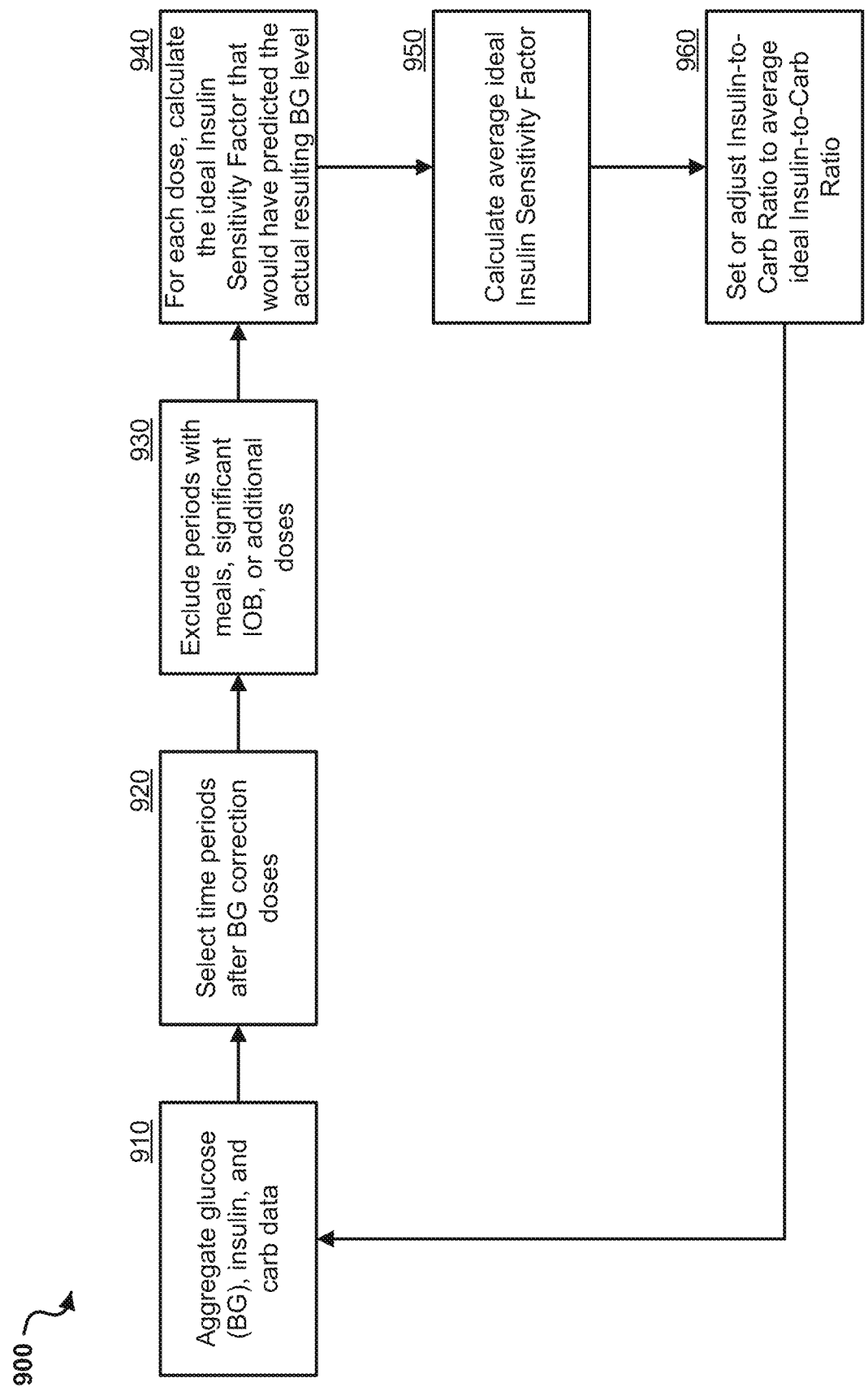
FIG. 9 shows a diagram of an example embodiment of a method for adjusting an insulin sensitivity factor parameter in accordance with the present technology.

FIG. 9 shows a diagram of an example method 900 for adjusting an insulin sensitivity factor parameter in accordance with the present technology. In various implementations, the method 900 can be implemented by the app associated with the pen device 10, which can include the modules of software architecture 200. The method 900 includes a process 910 to aggregate glucose data, insulin data, and carbohydrates data associated with a patient user. The method 900 includes a process 920 to select time period(s) after glucose correction dose(s). The method 900 includes a process 930 to exclude period(s) with meals, significant insulin on board (IOB) or additional doses. The method 900 includes a process 940 to calculate, for each dose, the ideal insulin sensitivity factor (IISF) that would have predicted the actual resulting glucose level. The method 900 includes a process 950 to calculate the average ideal insulin sensitivity factor (AIISF). The process 900 includes a process 960 to set or adjust the insulin sensitivity factor (ISF) to the average ideal insulin sensitivity factor (AIISF), e.g., based on the value calculated in the process 950. The determined ISF data from the process 960 can be feedback to the process 910 in implementations of the method 900.

Implementations of the subject matter and the functional operations described in this patent document can be implemented in various systems, digital electronic circuitry, or in computer software, firmware, or hardware, including the structures disclosed in this specification and their structural equivalents, or in combinations of one or more of them. Implementations of the subject matter described in this specification can be implemented as one or more computer program products, i.e., one or more modules of computer program instructions encoded on a tangible and non-transitory computer readable medium for execution by, or to control the operation of, data processing apparatus. The computer readable medium can be a machine-readable storage device, a machine-readable storage substrate, a memory device, a composition of matter effecting a machine-readable propagated signal, or a combination of one or more of them. The term "data processing unit" or "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Computer readable media suitable for storing computer program instructions and data include all forms of nonvolatile memory, media and memory devices, including by way of example semiconductor memory devices, e.g., EPROM, EEPROM, and flash memory devices. The processor and the memory can be supplemented by, or incorporated in, special purpose logic circuitry.

It is intended that the specification, together with the drawings, be considered exemplary only, where exemplary means an example. As used herein, the singular forms "a", "an" and "the" are intended to include the plural forms as well, unless the context clearly indicates otherwise. Additionally, the use of "or" is intended to include "and/or", unless the context clearly indicates otherwise.

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described and other implementations, enhancements and variations can be made based on what is described and illustrated in this patent document.

What is claimed is:

1. A system for determining a dose of a medicine to a patient, comprising:
    an injection pen device including a dose setting mechanism to set a dose of a medicine contained in a medicine cartridge that is to be dispensed by the injection pen device, a dispensing mechanism to dispense the medicine according to the set dose, and electronic circuits including a processor, a memory comprising instructions executable by the processor, and a wireless transmitter, the processor of the injection pen device configured to generate dose data associated with a dispensing event of a dose of the medicine dispensed from the injection pen device and time data associated with the dispensing event, and to wirelessly transmit the dose data;
    the injection pen device is in wireless communication with a mobile communication device that includes a data processing unit including a processor and memory to receive and process the dose data,
    wherein the mobile communication device includes a software application and a non-transitory computer-readable storage medium storing instructions, which when executed by the processor of the data processing unit, cause the mobile communication device to determine a recommended dose based on medicine data including dose data on one or more prior medicine doses, analyte data, and contextual data associated with a user of the injection pen device, wherein the contextual data includes physical activity data and/or nutrient data corresponding to a food,
    wherein the software application includes a data aggregator that obtains the analyte data and the contextual data, a dose calculator that autonomously determines the recommended dose of the medicine, and a user interface generator that produces a user interface on a display of the mobile communication device that displays, on the user interface, the recommended dose,
    wherein dose calculator autonomously modifies the determined recommended dose of the medicine when the determined recommended dose was not administered by the injection pen device in a predetermined time period from display of the recommended dose to qualify as a missed dose, and wherein the user interface generator produces the user interface to include:
        the medicine data, the analyte data, and the contextual data each represented by a value-time data plot having a time axis that is aligned with the time axis of the other value-time data plots;
        an indication of the missed dose displayed on the value-time plot representing the analyte data at a time along the time axis at which the recommended dose was displayed on the user interface; and
        a graphical representation, separate from the indication of the missed dose displayed on the value-time plot representing the analyte data, depicting a total number of missed doses, a dose type associated with the missed doses, and an indication of a time of day with which the missed doses are associated.

2. The system of claim 1, wherein the dose calculator is configured to determine when the missed dose occurred when an analyte level was within a target range at a time within or after the predetermined time period and thereby exclude the missed dose from calculation of the modified recommended dose.

3. The system of claim 1, wherein the dose calculator is configured to determine when the missed dose occurred when no nutrient data was registered at a time within or after the predetermined time period and thereby exclude the missed dose from calculation of the modified recommended dose.

4. The system of claim 1, wherein the dose calculator is configured to determine when the missed dose occurred based on the determined recommended dose being substantially zero and thereby exclude the missed dose from calculation of the modified recommended dose.

5. The system of claim 1, wherein the dose calculator is configured to determine a missed dose when glucose levels rise to a predetermined level change within a time period after a meal time.

6. The system of claim 1, wherein the indication of the missed dose includes a symbol on a single graph that includes a plot of the analyte data and a graphical indicator associated with the medicine data.

7. The system of claim 1, wherein the indication of the missed dose includes an amount of the missed dose on a single graph that includes a plot of the analyte data and a graphical indicator associated with the medicine data.

8. The system of claim 1, wherein the dose calculator is configured to calculate an amount of the missed dose based on a determined dose amount that would have corrected a resulting glucose level to a target level within a predetermined time period after the missed dose.

9. The system of claim 1, wherein the analyte data includes glucose levels, the medicine data includes insulin dose units, and the nutrient data includes a carbohydrate amount.

10. The system of claim 1, wherein the mobile communication device is implemented on a smartphone, a tablet, a wearable computing device including a smartwatch or smartglasses.

11. A system for tracking a dose of a medicine to a patient, comprising:
- an injection pen device configured to dispense a dose of a medicine;
- a mobile communication device configured to communicate with the injection pen device, the mobile communication device including a processor and a non-transitory computer-readable storage medium storing instructions, which when executed by the processor, cause the mobile communication device to:
  - autonomously determine a recommended dose of the medicine based on dose data associated with dispensing of the medicine from the injection pen device, analyte data associated with a user of the injection pen device, and carbohydrate intake data associated with the user of the injection pen device;
  - display the recommended dose of the medicine on a user interface of the mobile communication device; and
  - generate a report for display on the user interface of the mobile communication device, wherein the report includes:
    - an indication of a missed dose displayed on a value-time plot representing the analyte data at a time at which the recommended dose of the medicine was determined; and
    - a graphical representation, separate from the indication of the missed dose displayed on the value-time plot representing the analyte data, depicting a total number of missed doses, a dose type associated with the missed doses, and an indication of a time of day with which the missed doses are associated.

12. The system of claim 11, wherein the report further includes the dose data, the analyte data, and the carbohydrate intake data each represented by a value-time data plot having a time axis that is aligned with the time axis of the other value-time data plots.

* * * * *